US011510845B2

(12) United States Patent
Jensen et al.

(10) Patent No.: US 11,510,845 B2
(45) Date of Patent: *Nov. 29, 2022

(54) CPR TEAM PERFORMANCE

(71) Applicant: ZOLL Medical Corporation, Chelmsford, MA (US)

(72) Inventors: Jeffrey Paul Jensen, Winneconne, WI (US); Gary A. Freeman, Waltham, MA (US)

(73) Assignee: ZOLL Medical Corporation, Chelmsford, MA (US)

(*) Notice: Subject to any disclaimer, the term of this patent is extended or adjusted under 35 U.S.C. 154(b) by 972 days.

This patent is subject to a terminal disclaimer.

(21) Appl. No.: 15/349,099

(22) Filed: Nov. 11, 2016

(65) Prior Publication Data

US 2017/0112717 A1    Apr. 27, 2017

Related U.S. Application Data

(63) Continuation of application No. 13/474,269, filed on May 17, 2012, now Pat. No. 9,522,096.

(51) Int. Cl.
*A61H 31/00* (2006.01)
*A61N 1/39* (2006.01)
(Continued)

(52) U.S. Cl.
CPC .......... *A61H 31/005* (2013.01); *A61N 1/046* (2013.01); *A61N 1/3993* (2013.01);
(Continued)

(58) Field of Classification Search
CPC .............. A61H 31/005; A61H 2230/04; A61H 2201/5097; A61H 2201/5084;
(Continued)

(56) References Cited

U.S. PATENT DOCUMENTS 5,533,181 A    7/1996 Bergsneider
5,645,522 A *  7/1997 Lurie ..................... A61H 31/00
                                                            601/43
(Continued)

FOREIGN PATENT DOCUMENTS

CN    1458852 A    11/2003
CN    1723057 A    1/2006
(Continued)

OTHER PUBLICATIONS

Jeffcott, Shelley A., PhD et al., "Measuring team performance in healthcare: Review research and implications for patient safety". Journal of Critical Care (2008), 23, pp. 188-196.

*Primary Examiner* — Quang D Thanh
(74) *Attorney, Agent, or Firm* — The Webb Law Firm

(57) ABSTRACT

Systems and methods related to the field of cardiac resuscitation, and in particular to devices for assisting rescuers in performing cardio-pulmonary resuscitation (CPR) are described herein. A method for managing cardiopulmonary resuscitation (CPR) treatment to a person in need of emergency assistance includes monitoring, with an electronic medical device, a parameter that indicates a quality level of a CPR component being provided to the person by a user; determining, with the electronic medical device, that the parameter indicates that the quality level of CPR being provided is inadequate; and providing, to one or more rescuers of the person, an audible, visual, or tactile indication that a different person should perform the CPR component.

23 Claims, 12 Drawing Sheets

(51) Int. Cl.
  *A61N 1/04* (2006.01)
  *G09B 23/28* (2006.01)
  *G16H 20/30* (2018.01)

(52) U.S. Cl.
  CPC ........... *G09B 23/288* (2013.01); *G16H 20/30* (2018.01); *A61H 2201/5007* (2013.01); *A61H 2201/5015* (2013.01); *A61H 2201/5043* (2013.01); *A61H 2201/5048* (2013.01); *A61H 2201/5084* (2013.01); *A61H 2201/5097* (2013.01); *A61H 2230/04* (2013.01)

(58) Field of Classification Search
  CPC .... A61H 2201/5048; A61H 2201/5043; A61H 2201/5015; A61H 2201/5007; A61H 31/02; A61H 31/00; A61H 2230/505; A61H 2230/405; A61H 2230/205; A61H 2230/045; G09B 23/288; A61N 1/3993; A61N 1/046; G06F 19/3481; A61B 5/021; A61B 5/14542; A61B 5/6824; A61B 5/742; A61B 5/7405; A61B 2562/0219; A61B 5/024; A61B 5/7455; A61B 5/1118; A61B 2505/01; A61B 5/681; A61B 5/441; A61B 5/0402; A61B 5/026; A61M 16/0078; A61M 2016/003; A61M 2205/582; A61M 16/0084; A61M 2230/63; A61M 2230/62; A61M 2230/50; A61M 2230/432; A61M 2230/30; A61M 2230/205; A61M 2230/06; A61M 2205/8206; A61M 2205/80; A61M 2205/584; A61M 2205/581; A61M 2205/505; A61M 2205/3375; A61M 2205/332; A61M 2205/3306
  See application file for complete search history.

(56) References Cited

U.S. PATENT DOCUMENTS

| | | | |
|---|---|---|---|
| 6,930,715 B1 | 8/2005 | Mower | |
| 7,805,114 B1 | 9/2010 | Quintana et al. | |
| 2002/0133197 A1 | 9/2002 | Snyder et al. | |
| 2004/0015191 A1 | 1/2004 | Otman et al. | |
| 2004/0082888 A1 | 4/2004 | Palazzolo et al. | |
| 2004/0162585 A1 | 8/2004 | Elghazzawi et al. | |
| 2004/0267325 A1* | 12/2004 | Geheb | A61B 5/11 607/5 |
| 2006/0055786 A1 | 3/2006 | Ollila | |
| 2006/0056655 A1 | 3/2006 | Wen et al. | |
| 2006/0116724 A1 | 6/2006 | Snyder | |
| 2006/0173501 A1 | 8/2006 | Stickney et al. | |
| 2006/0187215 A1* | 8/2006 | Rosenberg | G06F 1/1626 345/173 |
| 2006/0290662 A1* | 12/2006 | Houston | A63F 13/06 345/156 |
| 2008/0171311 A1 | 7/2008 | Centen et al. | |
| 2009/0240295 A1 | 9/2009 | Kellum | |
| 2009/0270931 A1 | 10/2009 | Liden | |
| 2010/0022904 A1* | 1/2010 | Centen | A61H 31/005 600/534 |
| 2010/0211127 A1 | 8/2010 | Eerden | |
| 2010/0228165 A1* | 9/2010 | Centen | A61H 31/004 601/41 |
| 2010/0228166 A1* | 9/2010 | Centen | A61H 31/004 601/41 |
| 2010/0248679 A1 | 9/2010 | Oei et al. | |
| 2010/0256539 A1* | 10/2010 | Strand | A61M 15/0086 601/41 |
| 2011/0038114 A1* | 2/2011 | Pance | G06F 1/1673 361/679.4 |
| 2011/0117529 A1* | 5/2011 | Barash | G09B 23/288 434/265 |
| 2011/0117878 A1 | 5/2011 | Barash et al. | |
| 2011/0172550 A1 | 7/2011 | Martin et al. | |
| 2011/0210926 A1* | 9/2011 | Pasquero | G06F 1/1613 345/173 |
| 2012/0075464 A1 | 3/2012 | Derenne et al. | |
| 2012/0123224 A1* | 5/2012 | Packer | A61B 5/7405 600/301 |
| 2012/0195473 A1 | 8/2012 | De Haan et al. | |
| 2012/0330200 A1* | 12/2012 | Voss | A61H 31/004 601/41 |
| 2013/0138168 A1 | 5/2013 | Quan et al. | |
| 2015/0087919 A1 | 3/2015 | Johnson et al. | |

FOREIGN PATENT DOCUMENTS

| | | |
|---|---|---|
| CN | 1750857 A | 3/2006 |
| CN | 101001668 A | 7/2007 |

* cited by examiner

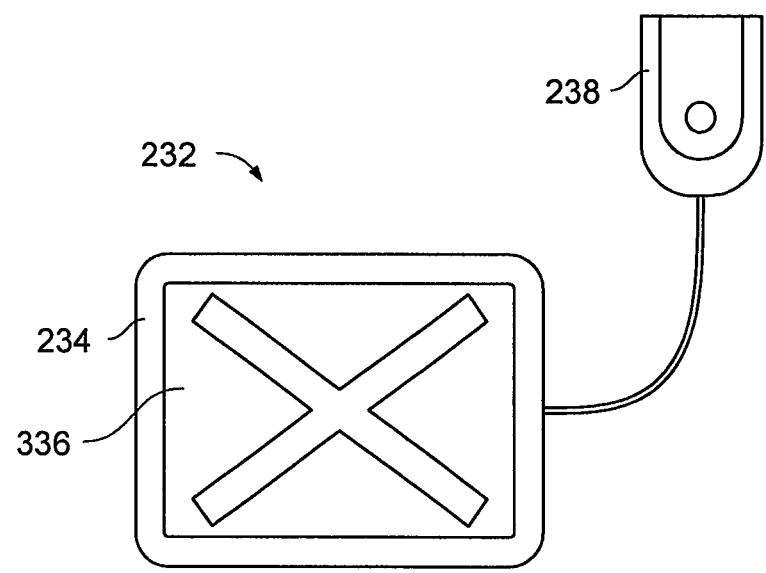
FIG. 2C
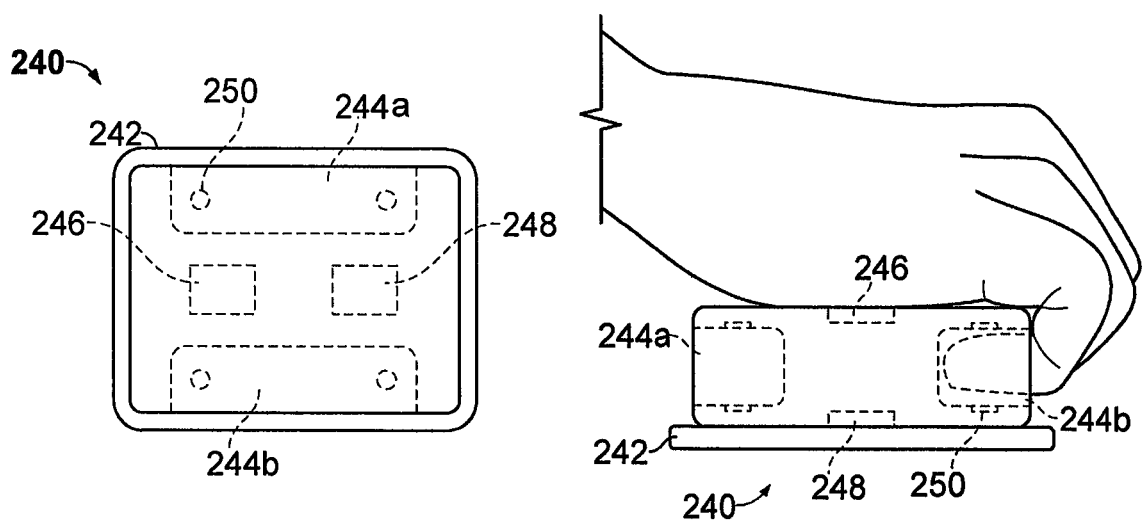
FIG. 2D
FIG. 2E

CPR TEAM PERFORMANCE

CROSS REFERENCE TO RELATED APPLICATION

This application is a continuation application of U.S. patent application Ser. No. 13/474,269, filed May 17, 2012, entitled "CPR Team Performance", which is herein incorporated by reference in its entirety.

TECHNICAL FIELD

This document relates to cardiac resuscitation, and in particular to systems and techniques for assisting rescuers in performing cardio-pulmonary resuscitation (CPR).

BACKGROUND

CPR is a process by which one or more rescuers may provide chest compressions and ventilation to a victim who has suffered an adverse cardiac event—by popular terms, a heart attack. Chest compressions are considered to be the most important element of CPR during the first five to eight minutes after CPR efforts begin, because chest compressions help maintain circulation through the body and in the heart itself, which is the organ that can sustain the most damage from an adverse cardiac event. Generally, American Heart Association CPR Guidelines define protocols by which a rescuer is to apply the chest compressions in coordination with ventilations. For example, current 2010 AHA Guidelines specify a ratio of 30:2 for compressions to ventilations—i.e., thirty compressions for every two breaths. And compressions are to be performed at a rate of around 100 per minute.

CPR may be performed by a team of one or more rescuers, particularly when the rescuers are professionals such as emergency medical technicians (EMTs) on an ambulance crew. One rescuer can provide the chest compressions and another can time their ventilations of the victim to match the chest compressions according to the appropriate CPR protocol. When professionals such as EMTs provide the care, ventilation is more likely to be provided via a ventilation bag that a rescuer squeezes, than by mouth-to-mouth. The CPR can be performed in conjunction with providing shocks to the patient from an external defibrillator, including from an automatic external defibrillator (AED) that is designed to be used by laypeople. Such AEDs often provide audible information to rescuers such as "push harder" (when the rescuer is not performing chest compressions forcefully enough), "stop CPR," "stand back" (because a shock is about to be delivered), and the like. In determining how chest compressions are being performed, certain defibrillators may obtain information from one or more accelerometers (such as in the CPR D PADZ, CPR STAT PADZ, and ONE STEP pads made by ZOLL MEDICAL of Chelmsford, Mass.) that can be used to compute depths of chest compression, e.g., to determine that the compressions are too shallow to be effective and thus to cause the verbal cue "push header" to be spoken by the defibrillator.

SUMMARY

This document describes systems and techniques that may be used to help manage the work by teams of rescuers who are responding to a victim, or person in need of emergency assistance. For example, typically such teams include a pair of rescuers, where a first of the rescuers performs CPR chest compressions on the victim and the other performs ventilations, either by mouth-to-mouth techniques or using a flexible ventilator bag. Frequently such teams are made up of an EMT or ambulance crew. Also frequently, a good heartbeat cannot be established quickly for the victim, so that CPR must be carried out for many minutes in order to maintain perfusion of blood in the victim. In such situations, rescuers can tire after only a minute or two of providing chest compressions, so that certain protocols call for the rescuers to switch roles periodically. The systems and techniques discussed here are implemented with a recognition that different people have different levels of skill, strength, and stamina for performing chest compressions and other components of CPR such as ventilating a victim or administering drugs to the victim. As a result, the techniques discussed here monitor the quality of certain components of CPR as it is being performed, such as by monitoring the depth and rate of chest compressions being performed, and they tell the rescuers to switch out when a component indicates that the performance of the chest compressions or other CPR component is inadequate, and might be, or would be, performed better by the other rescuer who is presumably more "fresh."

In certain implementations, such systems and technique may provide one or more advantages. For example, a patient may be provided with the best care that is available from the rescue team throughout a rescue episode. For example, a rescuer with greater stamina may be left performing chest compressions longer than another rescuer with less stamina, whereas they might have been allowed to perform for equal time periods, with substandard performance, using techniques other than those described here. Also, the terms of each cycle may change as the rescue continues—e.g., by shortening the cycles as each of the rescuers gets more tired. Such adjustments may be dynamic and need not rely on a static timed schedule. Also, the system may identify erosion in performance even when the rescuers themselves do not recognize that their performance has eroded. Such identification may occur by measures external to the rescuer, such as their rate and depth of providing chest compressions, or measures internal to the rescuer, such as by measuring their blood oxygen level and pulse rate. The instructions to switch may also be provided in a clear and simple manner (and in a variety of manners, such as audibly or on a visual display next to the hands of the rescuer performing chest compressions), so that even rescuers in a high-stress environment can get the message (and the instructions can be provided at an increasing severity level if the system determines that the rescuers are not responding to the original instructions). Moreover, in certain implementations, such techniques can be used on teams of two, three, or more rescuers. In addition, in certain implementations, the techniques described here can be implemented as part of an automatic external defibrillator (AED) or a professional defibrillator, or in a dual-mode defibrillator. As a result, the clinical performance of a rescuing team can be increased, and patient outcomes improved.

In one implementation, a method for managing cardio-pulmonary resuscitation (CPR) treatment to a person in need of emergency assistance is disclosed. The method includes monitoring, with an electronic medical device, a parameter that indicates a quality level of a CPR component being provided to the person by a user; determining, with the electronic medical device, that the parameter indicates that the quality level of CPR being provided is inadequate; and providing, to one or more rescuers of the person, an audible, visual, or tactile indication that a different person should perform the CPR component. The method may also comprise repeating cyclically the actions of monitoring, determining, and providing, while multiple different people are instructed to perform the CPR component. The CPR component can comprise chest compressions, and the parameter comprises depth of compression, rate of compression, or both. In some aspects, the method also comprises generating a chest compression quality score from a combination of chest compression rate and chest compression depth, and providing the indication in response to the quality score falling outside a determined acceptable range.

In certain particular aspects, the method further comprises providing information about a target chest compression depth with the electronic medical device, or providing periodic feedback to the user by displaying on a graphical display screen of the electronic medical device, an indication of values for depths of one or more of a plurality of chest compressions and an indication of a target compression depth. Providing the periodic feedback can also comprise displaying on a graphical display screen of a defibrillator, a graphical representation of the depths of one or more of the plurality of the chest compressions and an indication of the target compression depth. Separately, providing the periodic feedback can further comprise displaying on a graphical display screen of a defibrillator, a graph having a visual indicia representing the target compression depth and visual indicia representing the values for the depths of one or more of the plurality of the chest compression displayed above or below the visual indicia representing the target compression depth.

In yet Other aspects, the method can also comprise displaying, on a first electronic display located on a thorax of the person in need of emergency assistance, information that provides instructions for performing CPR to one of the rescuers. And display may be made, on a second electronic display and to another of the rescuers, of information that provides instructions for performing CPR to one of the rescuers, the information provided on the first electronic display differing from the information provided on the second electronic display. The electronic device can also be connected to a defibrillation electrode on the person in need of emergency assistance. Moreover, the method can include providing, to a first of the one or more rescuers, an indication about the quality of chest compressions given to the patient, the indication about the quality chest compressions differing from the indication that a different person should perform the CPR component. Yet in other implementations, the method comprises identifying a protocol for CPR being performed by the rescuers, and coordinating the providing of the indication that a different person should perform the CPR component with stored parameters that define the protocol, wherein the identified protocol is select from among multiple protocols stored on the electronic medical device.

In another implementation, a system is disclosed for managing cardiopulmonary resuscitation (CPR) treatment to a person in need of emergency assistance. The system comprises an electronic patient monitor; a sensor interface on the monitor arranged to receive input from one or more sensors that sense one or more that indicate a quality level of one or more CPR components being provided to the person in need of emergency assistance; a CPR monitor in the electronic patient monitor programmed to use the input from the sensors to identify a quality parameter and to generate a signal to switch rescuers performing CPR when the quality parameter meets a determined criterion; and an output interface in communication with the CPR monitor and arranged to provide rescuers using the electronic patient monitor with an indication to switch rescuers, in response to receiving the generated signal from the CPR monitor. The electronic patient monitor can be part of an external patient defibrillator, and the output interface can comprise an electronic display attached to a connector that also is attached to defibrillator electrodes for connection to the external patient defibrillator. Moreover the electronic display can be attached to one of the defibrillator electrodes and arranged so as to rest adjacent a rescuer's hands when the electrode is properly placed on the person in need of emergency assistance, and the rescuer's hands are placed for performing CPR chest compressions. In some aspects, the CPR monitor comprises a microprocessor connected to electronic memory that stores instructions that when executed perform a process of identifying a quality parameter and generating a signal to switch rescuers performing CPR when the quality parameter meets a determined criterion.

In some other aspects, the system also comprises a sensor arranged to sense a quality level of chest compressions performed on the person is need of emergency assistance. The CPR monitor can also be further programmed to repeat cyclically actions of identifying the quality parameter, determining whether the quality parameter indicates a need to switch rescuers, and generating a signal to switch rescuers when the quality parameter indicates a need. And the quality parameter can reflect a depth of chest compressions, rate of compression, or both, of chest compressions performed on the person in need of emergency assistance. The system can also comprise a display arranged to provide feedback to a rescuer indicating a way to improve the one or more CPR components. Moreover, the output interface can comprise a wireless transmitter arranged to communicate data regarding the one or more CPR components to a rescuer of the person in need of emergency assistance. In addition, the first interface can be arranged to communicate with a first display device for use by a first rescuer, and further comprising a second interface arranged to communicate with a second display device for use by a second rescuer, the second display device to communicate information about a CPR component that is different than information about a CPR component that is displayed on the first display device. Finally, the system can further comprise identifying a protocol for CPR being performed by the rescuers, and coordinating the providing of the indication that a different person should perform the CPR component with stored parameters that define the protocol, wherein the identified protocol is select from among multiple protocols stored on the electronic medical device.

Other features and advantages will be apparent from the description and drawings, and from the claims.

DESCRIPTION OF DRAWINGS

FIGS. 2C-2E show chest compression pucks that can capture information from a rescuer.

DETAILED DESCRIPTION

This description discusses systems and techniques for guiding the provision of care to a patient, such as the provision of CPR to a victim of cardiac arrest. For example, a portable electronic defibrillator may be provided to rescuers and may include common features for delivering defibrillating energy (a shock) to a victim of cardiac arrest through electrodes that may be placed on the torso of the victim. The defibrillator may also be provided with a mechanism for sensing the manner in which CPR chest compressions are performed on the victim, such as a puck or similar item that includes an accelerometer and may be placed under the hands of the person performing chest compressions and on top of the sternum of the victim. The defibrillator may use information from such an item to identify the depth and rate of chest compressions that are being performed by a rescuer, and may identify when such information indicates that the rescuer is tiring, such as when the depth of compressions is inadequate for a time period, and the rate of compressions begins to slow. Also, the system may look to internal factors of the rescuer such as pulse and blood oxygen level, in making the determination. When the defibrillator makes a determination that the chest compressions are inadequate due to fatigue on the part of the rescuer, the defibrillator may provide an indication to that rescuer that he or she should step away and allow another rescuer to perform chest compressions for a time. For example, where there are two rescuers, the other rescuer may have been providing ventilation to the victim using a ventilation bag, and may be simultaneously prompted to turn and provide chest compressions, while the first rescuer takes over operation of the bag.

Figure 1:
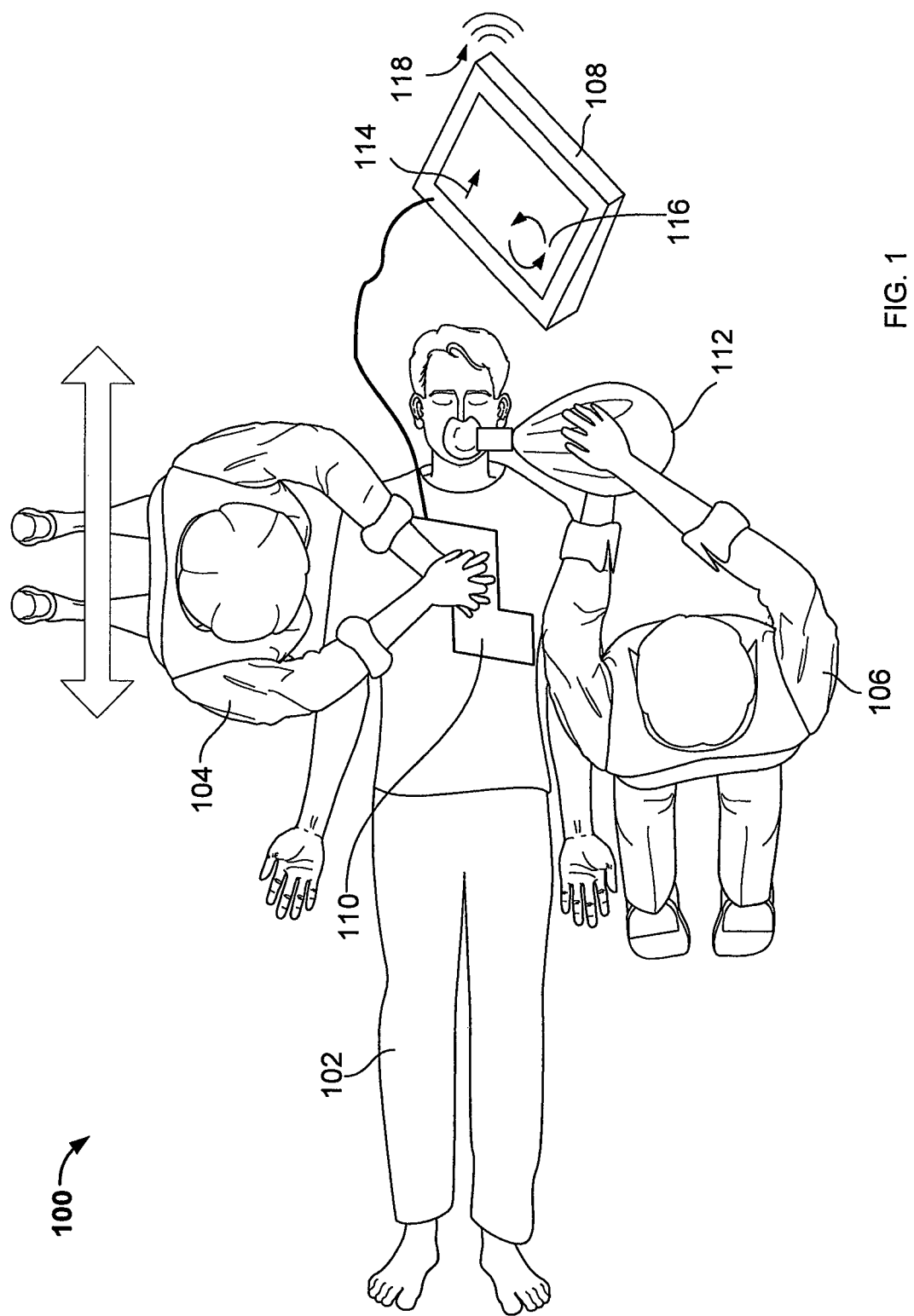
FIG. 1 is an overhead view of rescuers performing CPR on a victim using an electronic system that instructs them in performance of the CPR.

FIG. 1 is an overhead view of rescuers 104, 106 performing CPR on a victim 102 using an electronic system that instructs them in performance of the CPR. In this example, rescuers 104, 106 are already in position and providing care to the victim 102, with rescuer 104 in position and providing chest compressions to the torso of the victim 102, and rescuer 106 providing ventilation using ventilation bag 112. The rescuers 104, 106 may be lay rescuers who were in the vicinity of the victim 102 when the victim 102 required care, or may be trained medical personnel, such as emergency medical technicians (EMTs). Although two rescuers are shown here for purposes of explanation, additional rescuers may also care for the victim 102, and may be included in a rotation of rescuers providing particular components of care to the victim 102, where the components may include chest compressions, ventilation, administration of drugs, and other provision of care.

In some examples, one or more therapeutic delivery devices (not shown) can automatically deliver the appropriate therapy to the patient. The therapeutic delivery devices can be, for example, a portable automatic chest compression device (e.g., with a belt that wraps around the victim's chest), a drug infusion device, an automatic ventilator and/or a device that includes multiple therapies such as defibrillation, chest compression, ventilation, and drug infusion. The therapeutic delivery devices are physically separate from the defibrillator 108, and control of the therapeutic delivery devices may be accomplished by a communications link from the defibrillator 108 that may be wired, wireless, or both.

In other examples, control and coordination for the overall resuscitation event and the delivery of the various therapies may be accomplished by a device or processing element that is external to the defibrillator 108, such as by use of a tablet-based computer that is controlled by one of the rescuers. For instance, the device may download and process ECG data from the defibrillator 108; analyze the ECG signals, perform relevant determinations like those discussed above and below based on the analysis, and control the other therapeutic devices. In other examples, the defibrillator 108 may perform all the processing of the ECG, including analyzing the ECG signals, and may transmit to a separate device only the final determination of the appropriate therapy, whereupon the separate device can perform the control actions on the other linked devices.

An electrode assembly 110 is shown in position on the victim 102 in a normal position. The electrode assembly 110, in this example, is an assembly that combines an electrode positioned high on the right side of the victim's torso and an electrode positioned low on the left side of the victim's torso, along with a sensor package located over the victim's sternum. The sensor package, which is obscured in the figure by the hands of rescuer 104 in this example, may include an accelerometer or similar sensor package that may be used in cooperation with a computer in the defibrillator 108 to generate an overall quality score for the chest compression, and the quality score may indicate instantaneous quality or average quality across a time.

The score may indicate when and how the rescuer 104 is performing chest compressions on the victim 102, based on signals from the sensor package. For example, as a simplified description, signals from an accelerometer may be double integrated to identify a vertical displacement of the sensor package, and in turn of the sternum of the victim 102, to identify how deep each chest compression is. The time between receiving such input from the sensor package may be used to identify the pace at which chest compressions are being applied to the victim 102.

The defibrillator 108 in this example is connected to the electrode package 110 and may operate in a familiar manner, e.g., to provide defibrillating shocks to the electrode package 110. As such, the defibrillator may take a generally common form, and may be a professional style defibrillator, such as the R-SERIES, M-SERIES, or E-SERIES from ZOLL Medical Corporation of Chelmsford, Mass., or an automated external defibrillator (AED), including the AED PLUS, or AED PRO from ZOLL Medical Corporation. The defibrillator is shown in one position relative to the rescuers 104, 106 here, but may be placed in other locations to better present information to them, such as in the form of lights, displays, vibrators, or audible sound generators on a chest-mounted component such as an electrode or via an addressable earpiece for each of the rescuers. Such feedback, as discussed more fully below, may be on units that are separate from the main housing of the defibrillator, and that may communication information about the victim 102 and performance of CPR to the defibrillator 108 or may receive feedback information from the defibrillator 108, through either wired or wireless connects that are made directly with the defibrillator 108 or indirectly through another device or devices.

For illustrative purposes, two particular examples of feedback are shown here on a display of the defibrillator 108. First, a power arrow 114 provides feedback to the rescuer 104 regarding the depth of compression that the rescuer 104 is applying in each compression cycle to the victim 102. In this example, power arrow 114 is pointing upward, and thus indicating to rescuer 104, that rescuer 104 needs to apply more vigorous input to create deeper chest compressions. Such feedback may be only provided visually for performing chest compressions, in order to minimize the amount of information that the rescuer 104 must deal with in a stressful situation. For example, an arrow indicating to apply less compression may not be shown under an assumption that very few rescuers will apply too much compression, and thus the user need only respond to indications to apply more pressure. The particular type of feedback to be provided can be determined by a designer of the defibrillator 108 and may vary to match particular situations.

Separately, the rescuer 104 may be provided with additional limited feedback, such as feedback for performing chest compressions at an appropriate rate. As one example, the defibrillator 108 may emit a sound through speaker 118 in the form of a metronome to guide the rescuer 104 in the proper rate of applying CPR. A visual representation may also indicate rates for performing compressions, such as a blinking of the display on defibrillator 108. In addition, or as an alternative output mechanism that is designed to avoid distracting rescuer 106, haptic feedback may be provided to rescuer 104 through electrode assembly 110. For example, a puck or other item on which the rescuer 104 places her hands may be provided with mechanisms for vibrating the puck similar to mechanisms provided for vibrating portable communication devices (e.g., when an incoming telephone call is received on a smartphone). Such vibrating may be provided so as to minimize the amount of information that can distract other rescuers in the area, and may also more directly be used by the rescuer 104 to synchronize her chest compression activities with the output. For example, the vibrations may be periodic (approximate 100 times per minute) at the rate of performing chest compressions when the rescuer 104 should be performing compressions and may stop or be vibrated constantly when the rescuer 104 is to stop and switch positions with another rescuer, such as rescuer 106. With feedback provided at the rescuer's hands, and because the rescuer 104 is providing the chest compressions with her hands directly, input by the system into her hands may be more directly applied with respect to the rescuer 104 keeping an appropriate pace. Such haptic feedback may also relieve the rescuer 104 of having to turn her head to view the display on defibrillator 108. Thus, a first type of feedback, such as pulsed visual, audible, or tactile feedback may be provided to guide a user in performing CPR, and that type of feedback may be interrupted and replaced with a different type of feedback such as constant sound or vibration to indicate that a rescuer is to stop performing the particular component of CPR and let someone else take over.

Cycling arrows 116 are shown separately on the display of the defibrillator 108. Such arrows may indicate to the rescuer 104 and to the rescuer 106 that it is time for them to switch tasks, such that rescuer 104 begins operating the ventilation bag 112 (as shown by the arrow superimposed over the legs of rescuer 104 to indicate that she would slide upward toward the victim's head, rotate the bag 180 degrees and begin operating it), and rescuer 106 begins providing chest compressions on electrode assembly 110. Where there are three or more rescuers, the third rescuer may have been resting, and may take over chest compressions for rescuer 104 when a rescuer change is directed by the system, and the rescuer 104 may then the rest or may take the bag while rescuer 106 rests or does something else. For example, the rescuers may readily determine that rescuer 106 does not have the strength to provide consistent chest compressions on the victim 102, and may determine that rescuer 106 should constantly provide ventilation using ventilation bag 112, while other rescuers switch out in providing chest compressions. Thus, when the arrows 116 are displayed, rescuer 106 may stay in place while two other rescuers switch places with respect to delivering chest compressions. In the examples, discussed here, the system may be programmed to be indifferent to the manner in which rescuers decide to rotate, and the rotation may change during a rescue (e.g., rescuer 106 may initially provide chest compressions as part of a 3-person rotation and may then bow out and just provide ventilation while the other 2 rescuers rotate on chest compressions).

The defibrillator 108 may cause the cycling arrows 116 to be displayed based on the occurrence of various events. In one example, the cycling arrows 116 may be displayed after a set time period has elapsed since rescuer 104 began applying chest compressions. For example, a particular CPR protocol may require switching of rescuers at certain predefined periodic intervals (e.g., every 2 minutes). As described below in more detail, the cycling arrows 116 or a similar cycling signal, may alternatively be generated according to determinations made by the defibrillator 108 regarding the quality of chest compressions being provided to the victim 102 by rescuer 104, including by monitoring past compression parameters (e.g., rate over several compressions and depth) and monitoring the rescuer directly (e.g., by determining a pulse and blood oxygen level of a rescuer). Such an analysis may recognize that rescuers tire progressively over time as they are providing chest compressions, so that the depth of chest compressions is likely to fall over time, and the rate of chest compressions may also fall or become more erratic over time.

The defibrillator 108 may thus be programmed to identify when such factors indicate that the chest compression ability of the rescuer 104 has fallen, or is about to fall, below a level that is of adequate effectiveness. As discussed below, for example, a score may be generated for the depth of compression based on how far from optimal compression each of the rescuer's 104 compressions are. Another score may be generated based on how far from optimal the rate of compressions are, and the two scores (depth and rate) may be combined to generate an overall quality score for each compression. A third score may indicate the rescuer's 104 physical state (e.g., via pulse measurement) and that score may also be combined. A running quality score may then be computed to indicate the quality of compressions over a period of time, such as over the last several compressions made by the user, so as to better indicate a trend in the quality of chest compressions being provided (in the past, the near future, or both). When the quality score falls below a threshold, the defibrillator 108 may then generate an indication that the current rescuer 104 should stop performing chest compressions and allow someone else to take over, such as by displaying cycling arrows 116.

Similarly, the quality of ventilation may be monitored. For example, providers of ventilation may tire and forget that they are squeezing a ventilation bag too frequently—at too high a rate. They may be reminded initially, such as by a beeping metronome tied to the proper rate, or an LED on the bag that blinks at the proper rate. As with reminders for chest compression, such a reminder may be provided constantly, whether the user is performing properly or not, or can be triggered to start when the user is initially identified as performing in a substandard fashion. Subsequently, if the substandard performance continues for a predetermined time period or deteriorates to a second threshold level; the performance trends in a manner that indicates the user is not likely to improve the performance; or the performance otherwise indicates that the provider of ventilation should be switched out, a switching indication may be generated. Also, whether for compression or ventilation, different colors of lights may be used to indicate different types of feedback, such as a green light for good work, a yellow light to indicate a temporary deviation from good work, and a red light or even a blinking red light to indicate that the rescuer should switch out with someone else.

Where the providers of chest compressions and of ventilation are both being monitored in such a manner, a signal to switch may be generated when the first provider hits a substandard level. Alternatively, if chest compressions are considered more important than is ventilation, the level at which ventilation will trigger a switch can be set much more below a level considered to be satisfactory as compared to a level for chest compressions. In other words, a system may be biased to let the "weak" rescuer continue performing ventilation, rather than switching to a situation in which a somewhat fresh, but nonetheless tired with respect to squeezing a bag, and weak rescuer is placed in the most important position over another rescuer who may be more tired but is overall stronger at performing chest compressions. Various mechanisms may be used to balance the multiple factors, which include the relative important of each component to patient outcomes, the relative strength of each rescuer, the current performance and trending of performance for each rescuer, and knowledge or performance and trending for each rescuer from prior rescues (e.g., if the rescuers 104, 106 are part of an EMT team that uses the same defibrillator multiple times, or who have their data from multiple rescues uploaded to a central system for analysis) or prior cycles in the same rescue.

The process of observing the quality of a component of the CPR, such as the quality of chest compressions, may then continue recursively as long as care is being provided to the victim 102. For example, after the defibrillator 108 generates an indication to switch providers of chest compression, the defibrillator 108 may sense through the electrode package 110 that chest compressions stopped for a period, thus indicating that users have switched as suggested by the defibrillator 108. Once chest compressions then start again, the defibrillator 108 may again begin determining a quality score for chest compressions provided by the new rescuer, and may indicate that rescuers should switch again when the quality falls. In certain instances, an indication to switch may be blocked from being generated for a certain period after a new user begins performing compressions, under the assumption that the user might not be tired, but is merely trying to establish a rhythm in performing the chest compressions. Also, trends in the quality of the particular CPR component may be tracked rather than absolute values of the performance, so that the defibrillator 108 can distinguish situations in which a rescuer is giving a poor chest compressions because he or she was trying to find the appropriate rhythm or was distracted by a temporary problem, from situations in which the user truly is tiring and should be replaced.

In certain instances, the defibrillator 108 may be adaptable to different CPR protocols. For example, the defibrillator 108 may be programmed according to a protocol that, among other parameters, calls for each rescuer to provide chest compressions for a preset period of time. In such a situation, the defibrillator 108 may use pauses in the provision of chest compressions to determine when users have switched providing chest compressions, and may start a timer based on such observation. When the timer hits the preset period, the defibrillator 108 may then provide an indication that the rescuer giving chest compressions is to change. The timer may then be reset once a next rescuer is identified as having started giving chest compressions, such as by recognizing a pause in the provision of chest compressions.

Other protocols may be more flexible and may allow switches in rescuers to be dependent on the performance of the rescuers in addition to a predefined time interval. For example, the defibrillator 108 may be programmed to indicate that rescuers should change when it senses that performance has fallen below an acceptable level, and may also indicate the need for change when a maximum preset time has occurred even if the current rescuer appears to be performed well. In such a protocol, the time interval may be substantially longer than an interval for a protocol that requires changing based only upon elapsed time, and not upon degraded performance by the rescuer. Various different protocols may call for changing of rescuers based on different levels in performance, or upon different elapsed time periods, or a combination of the two. In particular, AHA protocols are generally just guidelines, and a particular medical director may alter such guidelines to fit their particular needs or professional judgment. (Indeed, revisions to AHA guidelines typically come from forward-thinking people who make modifications to prior guidelines and find the modifications to be effective.)

In such a situation, the defibrillator 108 may be programmed with the parameters for each of the protocols, and an operator of the defibrillator 108 may select a protocol to be executed by the defibrillator 108 (or the protocol may have been selected by a medical director). Such a selection may occur at the time of a rescue, or at a prior time. For example, the ability to select of a protocol may be limited to someone who logs onto the defibrillator 108 or configuration software separate from defibrillator 108 using administrator privileges, such as a person who runs an EMT service (e.g., a medical director of appropriate training and certification to make such a determination). That person may select the protocol to be followed on each of the machines operated by the service, and other users may be prevented from making such changes. In this manner, the defibrillator 108 may be caused to match its performance to whatever protocol its users have been trained to.

Thus, using the techniques described here, the defibrillator 108 may, in addition to providing defibrillation shocks, ECG analysis, and other features traditionally provided by a defibrillator, also provide indications to switch rescuers between various components of providing CPR and other care to a patient. The defibrillator may be deployed in the same manner as are existing defibrillators, but may provide additional functionality in a manner that can be easily understood by trained and untrained rescuers.

Figure 2B:
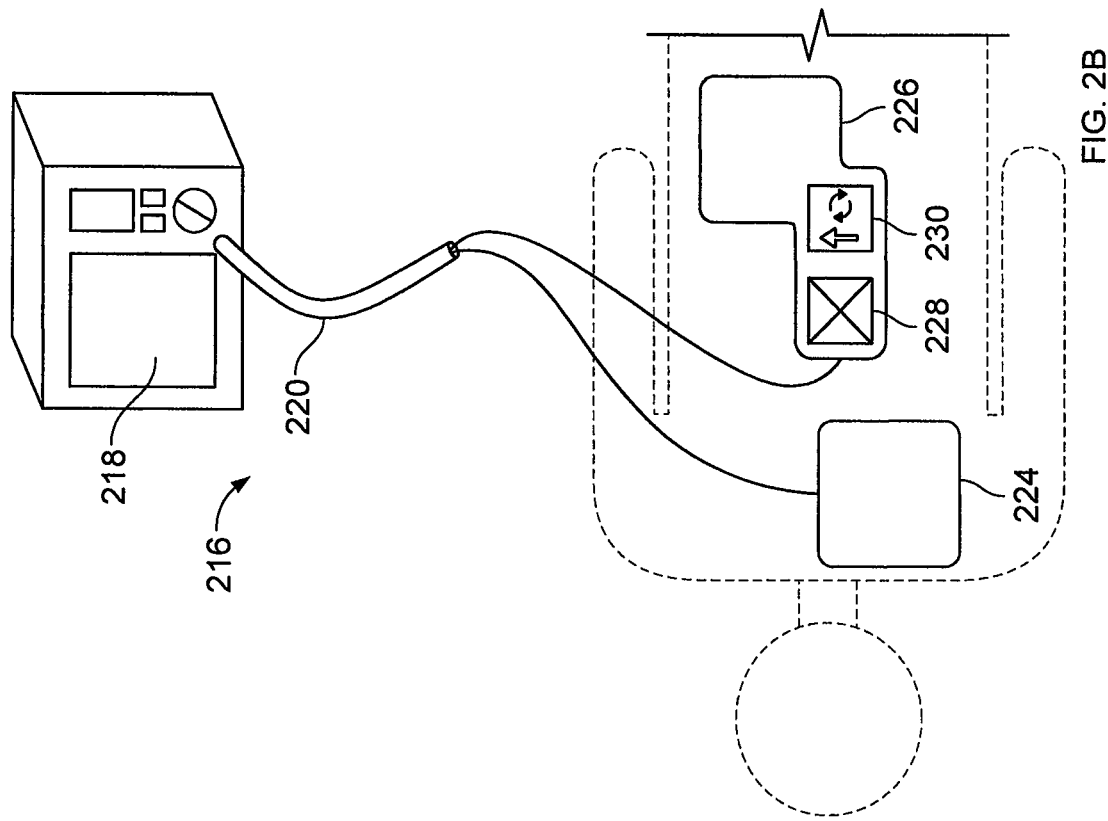
FIGS. 2A and 2B show a portable defibrillator and ancillary components arranged to provide feedback and instruction to rescuers.
Figure 2A:
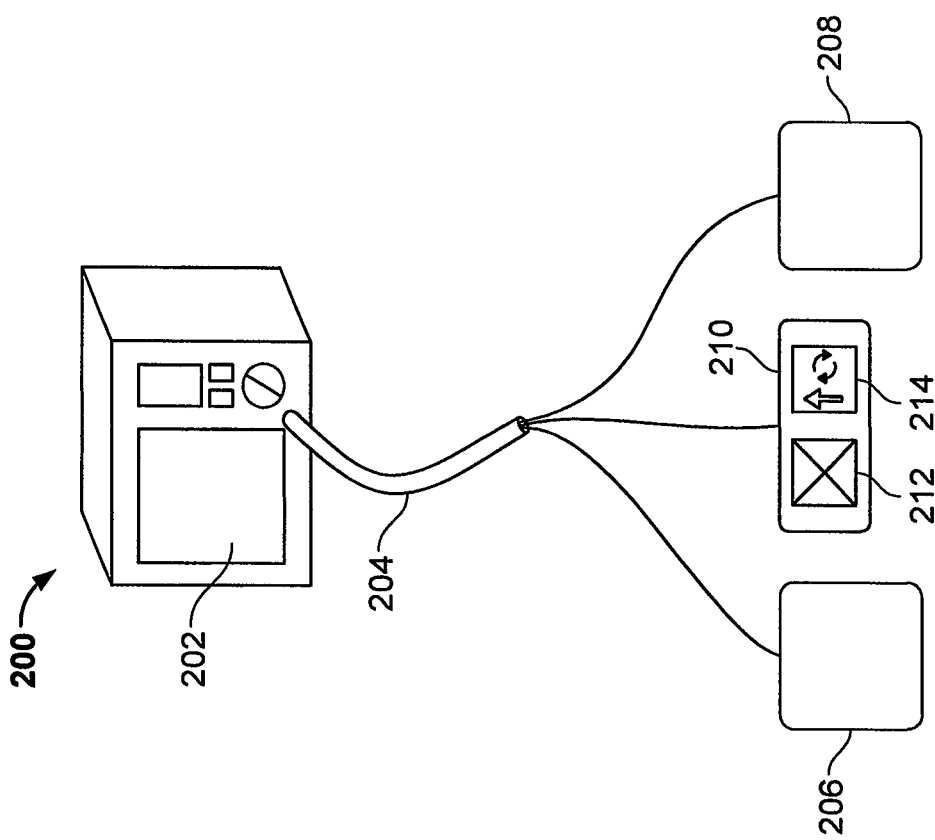

FIGS. 2A and 2B show a portable defibrillator and ancillary components arranged to provide feedback and instruction to rescuers. Each of the figures shows an example in which visual feedback can be provided to a rescuer from a location that is away from the defibrillator unit, and more immediately in the line of sight and focus of attention of a rescuer, such as a rescuer who is providing CPR chest compressions.

Referring to FIG. 2A, a system 200 is shown in which a defibrillator 202, which takes a standard form, but is provided with additional user feedback functionality, is connected to an electrode assembly by way of a wiring harness 204. The wiring harness 204 may include a number of wire leads that are connected together by a common plastic shroud that may surround the wires or may have been integrally formed around the wires such as through an extrusion process, and may be connected to the defibrillator 202 by way of a single plug. For example, the defibrillator 202 may be provided with a female or male connection, and the plug may be provided with a corresponding connection in a manner that is well known in the art. The wires may carry power from the defibrillator 202, such as current to provide a shock to a victim who is being provided with emergency care, or to the defibrillator 202, such as in the form of signals for generating ECG information, accelerometer information, and measurements of trans-thoracic impedance of a victim.

The electrode assembly in this example includes a first electrode 206, a second electrode 208, and a chest compression assembly 210. The first electrode 206 may be configured to be placed above the victim's right breast, while the second electrode 208 may be configured to be placed below the victim's left breast. During a rescue operation, printed insignia on one or both of the electrodes 206, 208 may indicate to a rescuer how to deploy the electrodes 206, 208, and where each of them should be placed. In addition, the defibrillator 202 may display such instructions on a graphical display and may also provide verbal instructions to supplement was is shown in the visual instructions, such as instructions for the sequential operation of the defibrillator.

The chest compression assembly 210, in this example, includes a detector 212 and a display 214. The detector 212 may include a plastic housing within which is mounted an accelerator assembly. The accelerator assembly may move with the housing as chest compressions are performed on a victim so that motion of the accelerometer matches motion of the victim's sternum. The detector 212 is shown in the figure as having an "X" printed on its top surface to indicate to the rescuer where to place his or her hands when delivering chest compressions to a victim. The accelerator in the housing may be connected to pass signals through harness 204 to defibrillator 202 (or may include a wireless transceiver for passing the information wirelessly), which may be provided with circuitry and or software for converting such signals into the indications about the rate and depth of compressions being performed on the victim, in manners such as those described below.

The display 214 may provide feedback that is directed to the rescuer who is performing chest compressions. In this example, the feedback comprises symbols similar to those shown on the display of defibrillator 108 in FIG. 1, in particular, an arrow indicating when the user is to perform chest compressions more vigorously, and circular cycling arrows indicating when rescuers are to switch in performing chest compressions. The particular symbols used may be selected also to be independent of the orientation from which they are viewed (as the cycling arrows are here), so that the symbols may have the same meaning to a rescuer who is on the right side of the victim as to a rescuer who is on the left side of the victim. In that manner, the system 200 does not need to determine where the rescuer is positioned. Also, a haptic vibrating mechanism may be provided at the assembly 210, so as to provide tactile beats or metronomes for a user to follow in providing chest compressions. In certain instances, when the unit indicates that rescuers are to switch, such haptic or tactile feedback may be turned off or provided as a constant vibration so as to provide an additional indication to the rescuer that they should no longer be performing chest compressions.

FIG. 2B shows a slightly different arrangement in a system 216 that includes a defibrillator 218 that is the same as defibrillator 202. In actual implementation also, the same defibrillator could be used with two different types of electrode assemblies like those shown here in FIGS. 2A and 2B. With specific reference to FIG. 2B, a wiring harness 220 in this example may be the same as wiring harness 204 in FIG. 2A, though here it connects defibrillator 218 to an electrode 224, and an assembly 226. The electrode 224 may simply be a single electrode that is connected to receive energy from the defibrillator 218, and is arranged to be placed in a conventional manner above a victim's right breast. The electrode 224 may also include mechanisms for sensing an ECG reading from a victim, and for communicating sensed parameters back to the defibrillator 218.

The assembly 226 may take a slightly L-shaped form, with one leg comprising an electrode designed to be placed below a victim's left breast, and another leg arranged to lie in a line with the victim's sternum. The assembly may be mounted on a flexible foam later that includes a gel layer on the bottom of the electrode for conducting a shocking pulse to a victim, but no gel under the sensor portion. However, the sensor portion may have a form of adhesive on its bottom side so that the accelerometer does not bounced and separate from the victim during chest compressions, and thus give an inaccurate reading to the defibrillator 218.

In this example, the hypothetical victim is shown in dotted lines to indicate how the electrode 224 and the assembly 226 may be positioned in actual use. Before they are deployed, however, the various electrodes and assemblies may be stored in a sealed packet, and the wires may be coiled to reduce needed space, in conventional manners. At the time of an emergency, the wires may have already been plugged into the defibrillator (e.g., via the wires extending through a sealed hole out of a packet in which the electrodes are stored to keep their gels moist). A rescuer can then open the package, plug the wires in if they are not already plugged in, and if necessary, read instructions on the back sides of the electrodes regarding the proper manner to apply the electrodes—e.g., with graphics that show the peeling off of covers over the electrode gels and also show images of the proper placement of the electrodes on a line-drawn victim.

In additional to electrodes, the assembly 226 may include a sensor assembly 228 and a display 230, similar to the sensor assembly 212 and display 214 in FIG. 2A. In addition, the components that provide functionality of the assembly 228 and display 230 may be the same as those described above for assembly 212 and display 214 in FIG. 2A. In this example, though, the assembly 228 and display 230 are connected directly to the electrode 226 by flexible structures that are arranged and sized so as to place the electrode and sensors in appropriate locations for a victim (under a left breast and aligned over the top of the sternum). Such an arrangement allows the system 216 to have fewer components that need to be applied to a victim then the system 200, while still having the flexibility to space the two electrodes relative to each other depending on the size of the victim— i.e., because the electrodes are separate from each other, it may be easier to position them both on small victims and very tall/long victims.

In both of the systems 200, 216, the placement of a display near the hands of a rescuer may provide one of more benefits in certain implementations. For example, a rescuer is typically looking at his or her hands when applying chest compressions, both because it is most natural to look forward, and as a mechanism to obtain feedback on how deep the chest compressions are and how the victim is doing. Thus, the rescuer can see the feedback without having to look around, and can constantly receive the feedback even while performing chest compressions. Also, the components can be provided in such locations conveniently and with relatively low cost, since the electrodes and accelerometers will already be provided, and a display need simply be added to one of these existing components (though in other implementations, the display may be located elsewhere). The feedback device also is naturally positioned to provide haptic feedback, which might be more directly processed by a rescuer. And by using visual feedback that is in the field of view of a particular rescuer and using haptic feedback, the system can reduce "attention pollution" at a scene, in that is lessens the level of noise and other distractions that other rescuers have to deal with in a very stressful environment.

Feedback devices away from the main medical device may also take other forms. For example, an LED may simply be provide in the top surface of one of the electrodes or near a puck, and the LED may blink to indicate a rate of chest compressions to be performed, and stay solid on to indicate that rescuers should switch positions. Also, an LED or graphical display may be provided on the ventilation bag 212, such as to blink to indicate a rate at which the bag is to be squeezed, and may be made solid in coordination with a display for the person performing chest compressions being made solid. In other words, the same signal can be provided to each of the rescuers to switch places, though on the respective sub-system that they are currently operating. As a result, the rescuers will only need to know a single "change" signal and will be able to react more intuitively and more quickly.

FIGS. 2C-2E show chest compression pucks that can capture information from a rescuer. In general, typical pulse oximetry sensor components may be integrated into a device on or in which a rescuer places his or her fingers, and can be used to provide a connected (wired or wirelessly) medical device such as a defibrillator, with indications of the blood oxygen level and pulse rate of a rescuer holding the device, which in these examples can be referred to as a CPR puck. The pucks shown here may be provided as part of the systems also shown in FIGS. 2A and 2B, such as by integrating the components for sensing rescuer condition into the components in those other figures.

Referring now specifically to FIG. 2C, there is shown an assembly 232 made up of a puck housing 336 and substrate 234. The substrate 234 may have on its lower side an gel-based adhesive so that the assembly 232 adheres to the chest of a victim on which it is placed. The housing 336 may in turn be solidly adhere to the top of the substrate 234 do that the housing 336 moves with a victim's sternum when a rescuer places his or her hands on top of the "X" shown on the top surface of the housing 236 and performs chest compressions. Connected to the substrate 234 and/or housing 336 by wire is a pulse oximeter 238. The pulse oximeter may report a blood oxygen level and pulse rate through the wire from which hit is attached into the remainder of the assembly 232, from which it may be reported to a defibrillator or other medical device, either wirelessly or by wired connection.

In operation, when a rescuer begins performing chest compressions, he or she may be instructed to slip a fingertip into the pulse oximeter 238 before placing his or her palms on top of the housing 336. The wire may permit movement of the rescuer's fingertip as they perform chest compressions, while measuring the relevant values. Such values may then be used, as discussed above, along with other factors such as rate and depth of compressions, to determine when the rescuer should be instructed to stop performing chest compressions and yield to another rescuer. Also, the assembly 232 may be provided as a stand-alone unit separate from a defibrillator or other medical, so as to provide more general feedback to a rescuer, where the feedback integrates consideration of rescuer blood oxygen level, pulse, or both.

Referring to FIGS. 2D and 2E, there is shown a top and side section view of an assembly 240 that is similar to assembly 232 in FIG. 2C, but integrates sensing functionality for the rescuer into the puck housing.

Again, the housing is shown on top of an adhesive substrate 242, but in this example, the housing is provided with depressions 244a, 244b into which a rescuer can slide his or her fingertips while performing chest compressions, as shown by the hand in FIG. 2E. The housing is provided here with depressions 244a, 244b on opposed sides, so that rescuers on both sides of a victim may use the assembly 240 and take advantage of its rescuer monitoring functionality. Also, as shown, sensors 250 can be provided at multiple locations, including four different locations to reflect rescuers who may be on either side of the victim and may places fingers from their right or left hands into the depressions 244a, 244b.

The assembly may simply send signals back to a medical device such as a defibrillator. Separately, the assembly 240 may modify or analyze the signals right on the assembly 240 in the housing. Thus, for example, a oximeter processor 248 is shown inside the housing and may receive signals from the sensors 250 and convert them partially or fully into blood oxygen and pulse rate values that can then be displayed or further processed on the assembly 240 (e.g., to identify that the rescuer is becoming fatigued). Similarly, an accelerometer pack 246 may be provided inside the housing in a position so as to sense proper motion of the victim's sternum. The pack 246 may, for example, compute depths of compressions and rates of compressions, and may also be connected to an output mechanism on the assembly 240 or connected to a medical device that is separate from the assembly 240 so as to provide chest compression feedback in manners like those discussed above and below.

Figure 3:
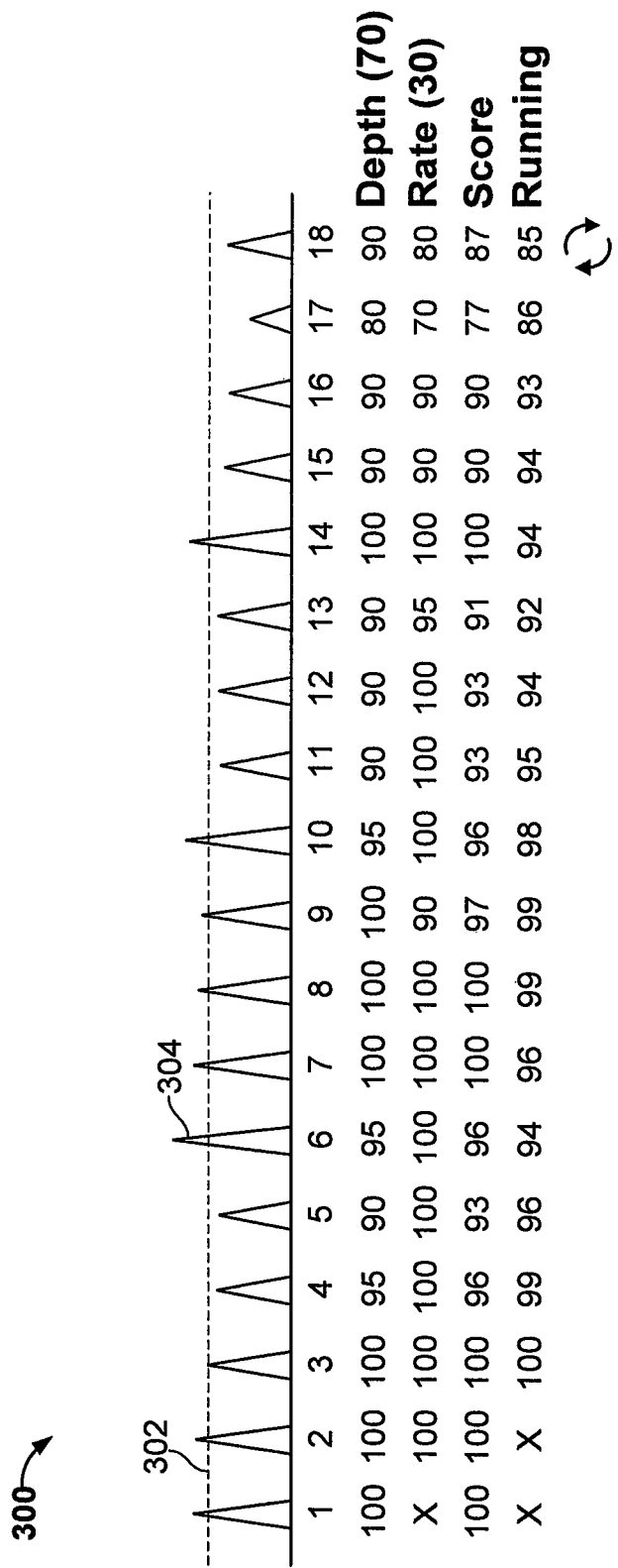
FIG. 3 shows example chest compression inputs and mechanisms for analyzing the inputs to determine whether a different person should provide chest compressions.

FIG. 3 shows example chest compression inputs and mechanisms for analyzing the inputs to determine whether a different rescuer should provide chest compressions. In general, the example here shows a series of eighteen chest compressions 300 that have been graphed along a horizontal time axis, along with a variety of numbers that represent parameters of how the chest compressions were performed. Such sensed compression data and derived numbers may then be used to determine when the quality of the chest compressions indicates tha the rescuer is getting fatigued, and the system should indicate to the rescuer that they should switch with another, fresher rescuer.

Referring more specifically to the graphed compressions, a dashed line 302 represents a target chest compression depth and each of the spikes 304 here indicate a distance level of downward compression (y axis), graphed according to time (x axis). In particular, the compressions are sharp motions followed by pauses, with the overall pattern repeated eighteen times during the time (which may be a fraction of a minute when the rescuer is performing about 100 compressions per minute). Such compressions may be sensed by an accelerometer assembly that is between the hands of the rescuer performing chest compressions and the sternum of the victim. Sensed signals may then be passed through a wiring harness to circuitry and software in a defibrillator or other medical device that can analyze the signals to identified compression depths and timing of the chest compressions.

As can be seen, the initial chest compressions are at an appropriate level and an appropriate rate, but began to dip at the fourth and fifth compressions. The compressions then pick up and hit the dashed line 302, perhaps because the fall in compressions caused a defibrillator to indicate to a rescuer that they should compress harder, and the user followed such direction. The depth of compressions over time then falls again at compressions 11, 12 and 13, but then picks up at 14 and falls yet again near the end, indicating that the user has become fatigued.

Below the graph are shown numbers that, for this example, indicate values that may be computed by a defibrillator that is connected to a system for determining when to signal that a provider of chest compressions to a victim should be changed by the system. The top row shows a score that may be given to a user to rate the quality of the depth of the chest compressions. Such a score may be given a baseline of 100 around a depth that approximates the desired line of 302. The score may fall the further one gets from line 302, though the score may fall more quickly for deviations on the under-compression side than the over-compression side, e.g., if a determination is made that under-compression is a more serious error than over-compression. Thus, for example, the fifth compression falls below line 302 by an amount less than the sixth compression falls above the line, but the fifth compression receives a lower score than does the sixth compression.

In this example, the depth of compression factor is provided 70% of a weighting in determining an overall score for the quality of the chest compression. The other 30% of the score is driven by the rate at which the user provides the compressions. Thus, for example, one can see fairly even spacing for compressions two through eight, but a slight delay for compression nine, so that the ninth compression receives a score of 90 instead of a score of 100. In addition, one can see lengthening delays between compressions at the end of the period. The rate scores reflect, in each instance, how far a compression was performed from the time at which it was supposed to be performed according to protocol. Again, the scores are scaled to a maximum of 100 for ease of explanation, but could take other forms also.

The third line in the numbers indicates an overall score for each of the compressions, where the overall score is simply the combined weighted value of the two component scores for depth and rate, respectively. Finally, the fourth line shows a running score that is a running average of the current score and the two previous scores. By using a running average, singular deviations from a perfect compression may be ignored, while lingering deviations can be captured so that continual failure by a user, which indicates fatigue of the user, can result in the generation of a signal to switch users in performing chest compressions. Thus, for example, compression number five is a bad compression, but the running score is relatively high because the previous two compressions were better.

In this example, the trigger for generating an indication that users should change position is a running score at or below 85. Thus, although the running score in the example rises and falls as a user has periodic problems with performing compressions, it does not fall to the triggering level until compression eighteen, after there had been three weak compressions in a row that were also spaced too far apart—so that the running average score really fell. In actual implementation, software may monitor the value as a user provides compressions, may periodically update the value (e.g., once for each compression or on another basis), and may cause a defibrillator, such as defibrillator 108, to emit output to one or more rescuers to indicate the need for a change, such as the indication shown in the prior figures above.

While the particular running average scoring technique described here is provided for its simplicity and ease of understanding, different approaches may be used to identify when a user is likely becoming too fatigued to maintain quality chest compressions or other components of CPR. For example, various inputs may be subjected to derivations in order to determine rates of change of those inputs. An indication to change rescuers may be generated when the rate of change in the quality of performance exceeds a preset amount in a negative direction. Also, models may be generated to represent fatigued users, and actual inputs may be compared to such models to indicate when fatigue is setting in for a real user and to cause an alert to be generated.

In certain instances, such as when the number of rescuers is known, data may be stored across multiple cycles of chest compression sessions for each of the users. For example, the system may identify in early cycles of a rescue that one of the rescuers has a sudden drop-off in chest compression performance but then recovers, and may store such understanding and use it in subsequent cycles so as to not trigger an indication to change rescuers simply because the particular rescuer is having momentary problems. Another rescuer may be seen to have a slower drop in performance but may be more erratic in his provision of chest compressions, so that a system may permit more variability before it triggers an indication to switch rescuers, since variability by that user may not indicate fatigue, but may simply be normal variability in the manner in which the user performs chest compressions. Other factors may also be taken into account in addition to depth and rate of providing chest compressions. For example, a heart rate monitor may be applied to a rescuer and an increase in heart rate may indicate fatigue by the rescuer, and may be used to generate a signal to switch rescuers. Also, the shape of a compression profile may be used, such that a jerky or sharp profile may indicate fatigue by a user, and also contribute to the triggering of a signal to switch rescuers.

Figure 4:
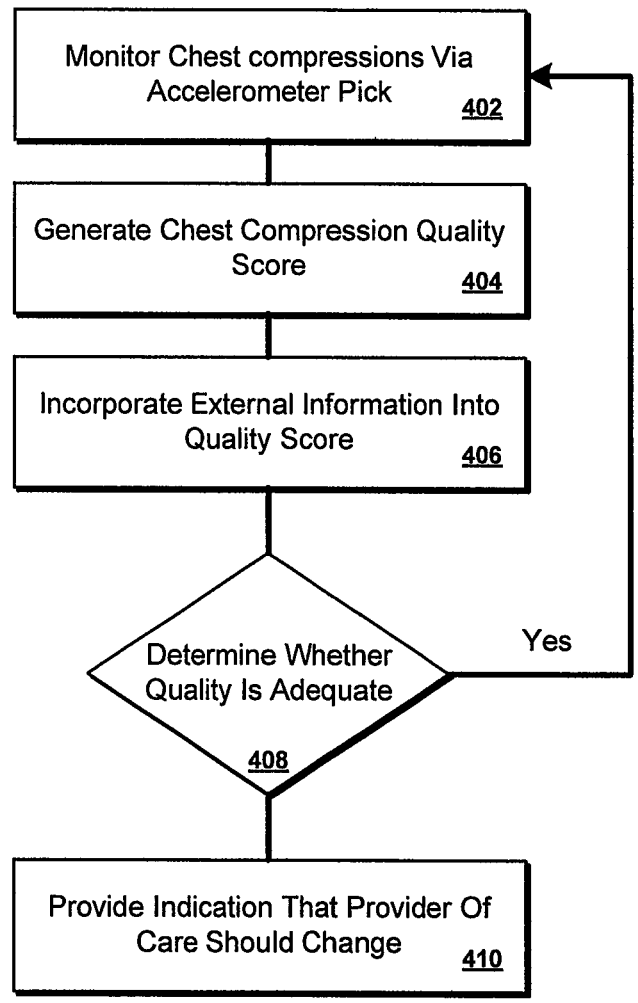
FIG. 4 is a flowchart of a process for monitoring CPR performance and providing feedback for improvement of the performance.

FIG. 4 is a flowchart of a process for monitoring CPR performance and providing feedback for improvement of the performance. Generally, the process involves automatic monitoring of the performance of a component of CPR, such as the provision of chest compressions to a victim, and the indication to a provider of such component when they should stop performing the component and allow another rescuer to perform the component.

The process begins at box 402, where the process monitors, using an accelerometer puck, chest compressions that are performed on a victim. The process may have been started after rescuers arrived at the scene of a victim and deployed electrodes and the puck onto the torso of the victim. The rescuers may have then turned on a defibrillator connected to the electrodes and puck, and the defibrillator may have begun performing relevant functions for the rescue, while the rescuers performed their manual functions. For example, the defibrillator may have initially began taking an ECG reading from the victim and displaying it to the rescuers on a graphical display, and may have analyzed the victim's heart rhythms to determine whether a shockable rhythm existed so that a defibrillating shock could be applied to the victim. Other relevant analysis and processing may also have been performed, and continue to be performed by the defibrillator.

At the same time, one rescuer may have applied the electrodes and the puck and have begun performing chest compressions on the victim. Such compressions may cause the puck to move and accelerate up and down, so that an accelerometer in the puck generates signals indicative of such acceleration. The defibrillator may receive such signals and convert them into indications of the quality of the chest compression, such as indications of how deep each test compression is, and the pace at which particular ones of the chest compressions are occurring. The other rescuer may separately have applied a ventilation bag to the victim's mouth and began squeezing the bag in coordination with the chest compressions according to a predetermined protocol.

Before the monitoring begins, the process may have gathered certain data to aid in the monitoring. For example, as a rescuer sets up a defibrillator and hooks it to a victim, the defibrillator may ask the rescuer (on a display or via a spoken request) whether the rescuer is alone or is being aided, and might also ask how many additional rescuers are available. If the rescuer indicates that he or she is alone, then the system may follow a branch of programming that does not recommend switching of rescuers, but might more aggressively provide feedback in order to overcome the extra fatigue a solo rescuer will face. If the rescuer is accompanied, then the system may subsequently indicate when rescuers are to switch roles. The system may also assign a label to each rescuer, such as "Rescuer 1" and "Rescuer 2" or the actual names of the rescuers (which could have been programmed previously, such as for EMTs who use the system frequently, or could be obtained, such as by lay rescuers speaking their names into the device in response to prompts from the device). If there are three or more rescuers, instructions for rotating may be more complex—i.e., involving more than simply an instruction to switch positions, but instead telling each rescuer what component of CPR they should be performing for any particular time period.

A determination about the number of rescuers may also be made inferentially. For example, a ventilation bag may include electronics that report to a defibrillator or other box, and the box may sense that the bag is being deployed or used, or is being used simultaneously with chest compressions being performed, in order to infer that there are at least two rescuers. The defibrillator may adjust its operation accordingly in the manners discussed above in such a situation (e.g. by enabling prompts for rescuers to switch roles).

At box 404, the process generates a chest compression quality score based on the observed prior chest compressions. For example, the quality score may be computed as a function of the depth and rate of one or more chest compressions that have been observed from the accelerometer puck. One such mechanism for computing a quality score is shown with respect to FIG. 3 above.

At box 406, external information is incorporated into the quality score, meaning that the information is external to the parameters that are indicating the current quality with which a particular component of CPR is being performed. With respect to chest compressions, the external components may include a pulse rate or respiration rate of a rescuer, indications about how that rescuer's performance degraded in prior sessions, predetermined time limits for the performance of chest compressions that may trump even adequate performance by a rescuer, and other such factors. Such an external factors may override the generated quality score, or may be incorporated into the quality score, such as to push it upward or downward depending on what the external factor is. For example, if the rescuer's pulse is abnormally high, the process may indicate that a new rescuer should take over chest compressions in response to an observed decrease in performance, in a manner that is more speedy than if the rescuer were observed to be calmer.

At box 408, a determination is made with regard to whether the quality of the performance of the CPR component is adequate or not. With respect to chest compressions, adequate quality may largely be a function of the depth of chest compression and also a function of the rate of compression (though to a lesser degree). Other CPR component may have their quality determined using other factors and parameters. The overall quality level may be expressed as a threshold number, a threshold rate of change, or other appropriate threshold, which need not be a constant threshold, but could instead be a threshold that changes over time also.

If the quality is determined to be adequate, the process returns back to box 402 and continues monitoring the chest compressions using the accelerometer puck and determining the quality of such compressions.

If the quality is determined to not be adequate, at box 410, the process provides an indication to the rescuer, and perhaps to others, than a provider of care should change. For example, the defibrillator may beep multiple times to indicate that a change in rescuers should occur between the tasks or components of chest compressions and operating the ventilation bag. Alternatively or in addition, visual indications may be given on a display of a defibrillator or may be displayed on a device mounted closer to the location where the rescuer is performing the particular component of CPR, such as adjacent to the hands of the rescuer when the hands are pressing on the sternum of a victim. In addition, haptic feedback may be provided to the rescuer, such as switching from periodic (metronomic) vibration in a unit under the rescuer's hands, to continuous vibration under the rescuer's hands, or another change in haptic feedback that differs from the feedback given when no change is to be made.

Using such a process, then, a system may adjust to the capabilities of various caregivers and maintain caregivers in a position to provide a particular component of care as long as they are able to provide for it. As a result, the system need not be stuck to preset time limits that might not reflect the actual standard of care that can be provided, but can instead vary based on the actual standard of care that is being given by a particular rescuer team in a particular situation. The process could result in better outcomes for victims tended to by such rescuers, and in a better experience for the rescuers themselves.

In certain circumstances, prompts for performing CPR may change the way in which CPR is to be performed in response to indications that there has been a degradation in performance. In particular, prompting of CPR at a sub-optimal level may be provided, as long as that sub-optimal level is better than wholly fatiguing a rescuer. For example, hemodynamics data indicates that depth of chest compressions may be more important to, victim well-being than is rate of compressions—i.e., it may essentially not matter how fast you are performing compressions if none of those compressions is truly effective. As a result, the system may slow a rate (e.g., a metronome) of prompting compressions and may monitor how the depth of compressions changes in response to the prompted change in rate. Using stores hemodynamic data correlating depths and rates to effectiveness, the system may identify a most-preferred rate that maximizes the hemodynamic effect for a particular rescuer (using, e.g., the well-known Windkessel model or other approach). While such modifications may be made only after sensing that a particular rescuer is fatiguing, they can also be initiated at other points and in response to other criteria, including by making such adjustments throughout a rescue cycle (e.g., the rate of a metronome may be adjusted slightly and essentially continuously, and the combination of depth and rate that is measured from the rescuer may be input in real-time to a formula for computing hemodynamic effect, with subsequent changes in the rate of the metronome being made in an attempt to increase the hemodynamic effect within bounds of safety).

Figure 5A:
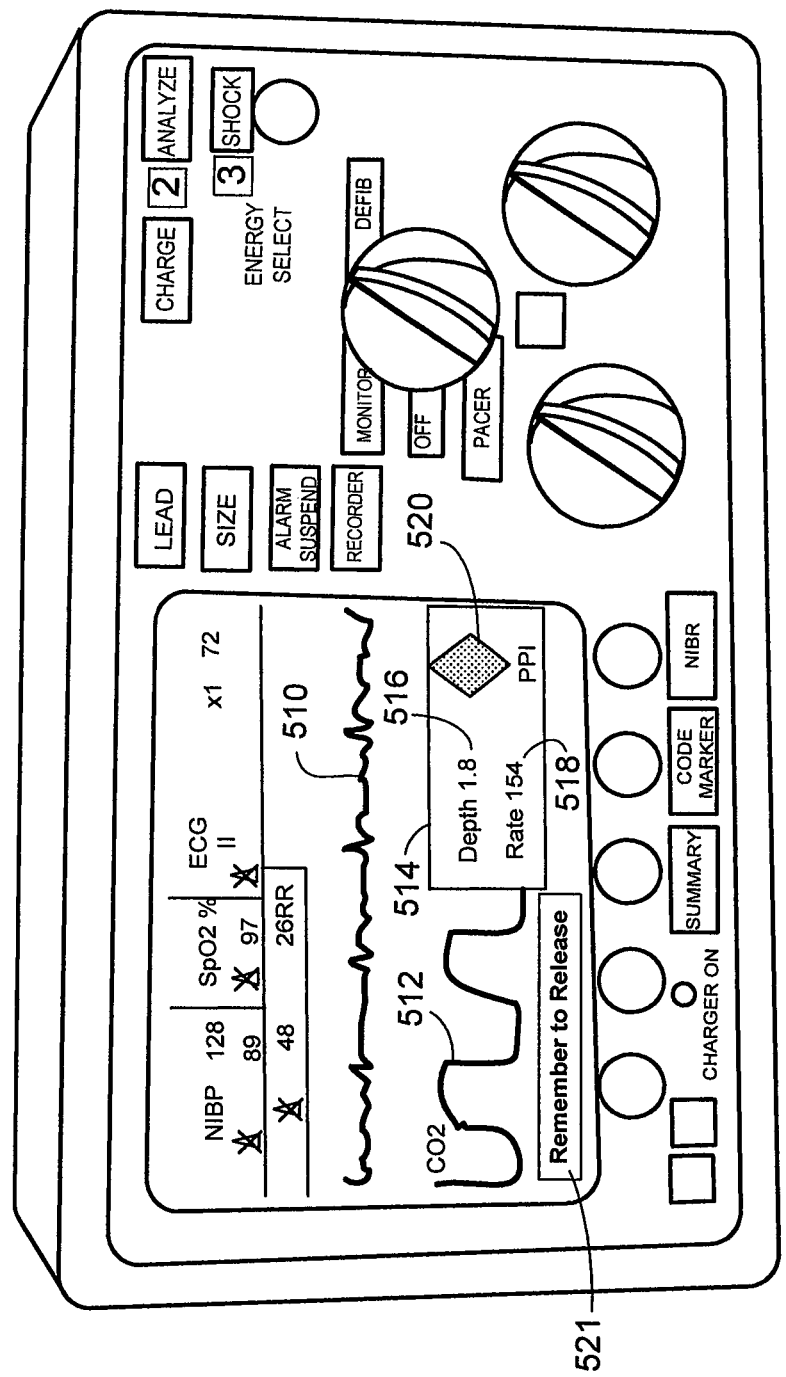
FIGS. 5A and 5B illustrate a defibrillator showing certain types of information that can be displayed to a rescuer.

FIG. 5A shows a defibrillator showing certain types of information that can be displayed to a rescuer. In the figure, a defibrillation device 500 with a display portion 502 provides information about patient status and CPR administration quality during the use of the defibrillator device. As shown on display 502, during the administration of chest compressions, the device 500 displays information about the chest compressions in box 514 on the same display as is displayed a filtered ECG waveform 510 and a CO2 waveform 512 (alternatively, an SpO2 waveform can be displayed).

During chest compressions, the ECG waveform is generated by gathering ECG data points and accelerometer readings, and filtering the motion-induced (e.g., CPR-induced) noise out of the ECG waveform. Measurement of velocity or acceleration of chest compression during chest compressions can be performed according to the techniques taught by U.S. Pat. No. 7,220,335, titled Method and Apparatus for Enhancement of Chest Compressions During Chest Compressions, the contents of which are hereby incorporated by reference in their entirety. Displaying the filtered ECG waveform helps a rescuer reduce interruptions in CPR because the displayed waveform is easier for the rescuer to decipher. If the ECG waveform is not filtered, artifacts from manual chest compressions can make it difficult to discern the presence of an organized heart rhythm unless compressions are halted. Filtering out these artifact can allow rescuers to view the underlying rhythm without stopping chest compressions.

The CPR information in box 514 is automatically displayed when compressions are detected by a defibrillator. The information about the chest compressions that is displayed in box 514 includes rate 518 (e.g., number of compressions per minute) and depth 516 (e.g., depth of compressions in inches or millimeters). The rate and depth of compressions can be determined by analyzing accelerometer readings. Displaying the actual rate and depth data (in addition to, or instead of, an indication of whether the values are within or outside of an acceptable range) can also provide useful feedback to the rescuer. For example, if an acceptable range for chest compression depth is 1.5 to 2 inches, providing the rescuer with an indication that his/her compressions are only 0.5 inches can allow the rescuer to determine how to correctly modify his/her administration of the chest compressions (e.g., he or she can know how much to increase effort, and not merely that effort should be increased some unknown amount).

The information about the chest compressions that is displayed in box 514 also includes a perfusion performance indicator (PPI) 520. The PPI 520 is a shape (e.g., a diamond) with the amount of fill that is in the shape differing over time to provide feedback about both the rate and depth of the compressions. When CPR is being performed adequately, for example, at a rate of about 100 compressions per minute (CPM) with the depth of each compression greater than 1.5 inches, the entire indicator will be filled. As the rate and/or depth decreases below acceptable limits, the amount of fill lessens. The PPI 520 provides a visual indication of the quality of the CPR such that the rescuer can aim to keep the PPI 520 completely filled.

As shown in display 500, the filtered ECG waveform 510 is a full-length waveform that fills the entire span of the display device, while the second waveform (e.g., the CO2 waveform 512) is a partial-length waveform and fills only a portion of the display. A portion of the display beside the second waveform provides the CPR information in box 514. For example, the display splits the horizontal area for the second waveform in half, displaying waveform 512 on left, and CPR information on the right in box 514.

The data displayed to the rescuer can change based on the actions of the rescuer. For example, the data displayed can change based on whether the rescuer is currently administering CPR chest compressions to the patient. Additionally, the ECG data displayed to the user can change based on the detection of CPR chest compressions. For example, an adaptive filter can automatically turn ON or OFF based on detection of whether CPR is currently being performed. When the filter is on (during chest compressions), the filtered ECG data is displayed and when the filter is off (during periods when chest compressions are not being administered), unfiltered ECG data is displayed. An indication of whether the filtered or unfiltered ECG data is displayed can be included with the waveform.

Also shown on the display is a reminder 521 regarding "release" in performing chest compression. Specifically, a fatigued rescuer may begin leaning forward on the chest of a victim and not release pressure on the sternum of the victim at the top of each compression. This can reduce the perfusion and circulation accomplished by the chest compressions. The reminder 521 can be displayed when the system recognizes that release is not being achieved (e.g., signals from an accelerometer show an "end" to the compression cycle that is flat and thus indicates that the rescuer is staying on the sternum to an unnecessary degree). Such a reminder can be coordinated with other feedback as well, and can be presented in an appropriate manner to get the rescuer's attention. The visual indication may be accompanied by additional visual feedback near the rescuer's hands, and by a spoken or tonal audible feedback, including a sound that differs sufficiently from other audible feedback so that the rescuer will understand that release (or more specifically, lack of release) is the target of the feedback.

Figure 5B:
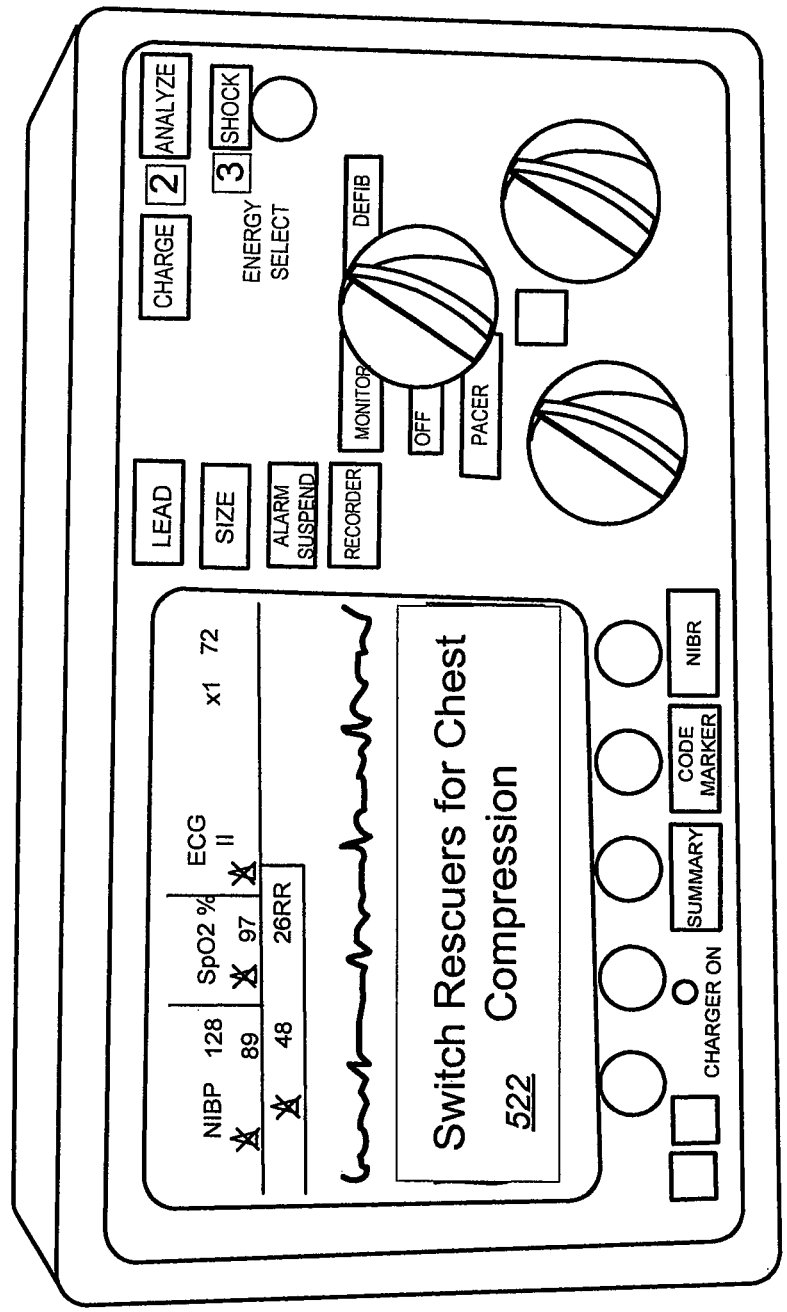

FIG. 5B shows the same defibrillator, but when performance of chest compressions has fallen below a determined quality standard. In this example, an alert box 522 is now shown across the bottom half of the display and over the top of information that was previously displayed to provide feedback to cause the rescuer to improve their administration of chest compressions. While the user can continue to perform chest compressions, the blockage of feedback information may further induce the fatigued user to stop performing chest compressions, and the information is more likely to be observed quickly by the rescuer since it is placed in an area on the display where the rescuer will already be looking for feedback.

Figure 6A:
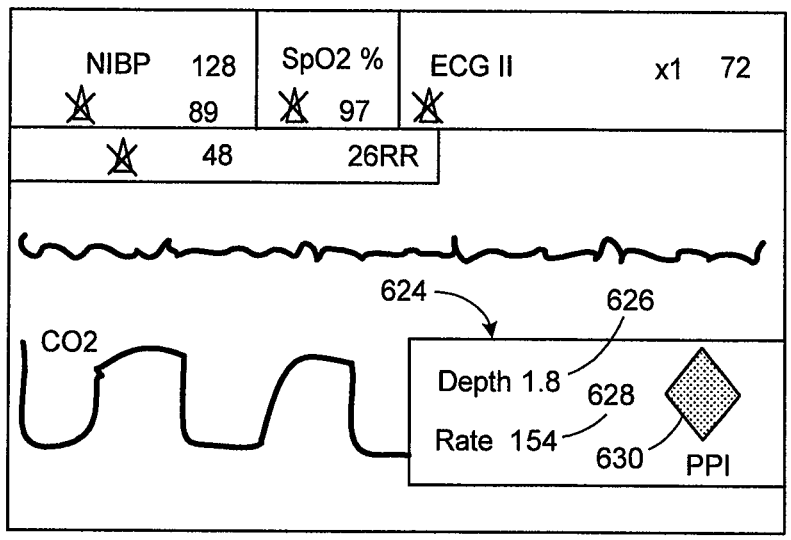
FIGS. 6A-6C show screenshots of a defibrillator display that provides feedback concerning chest compressions performed on a victim.
Figure 6B:
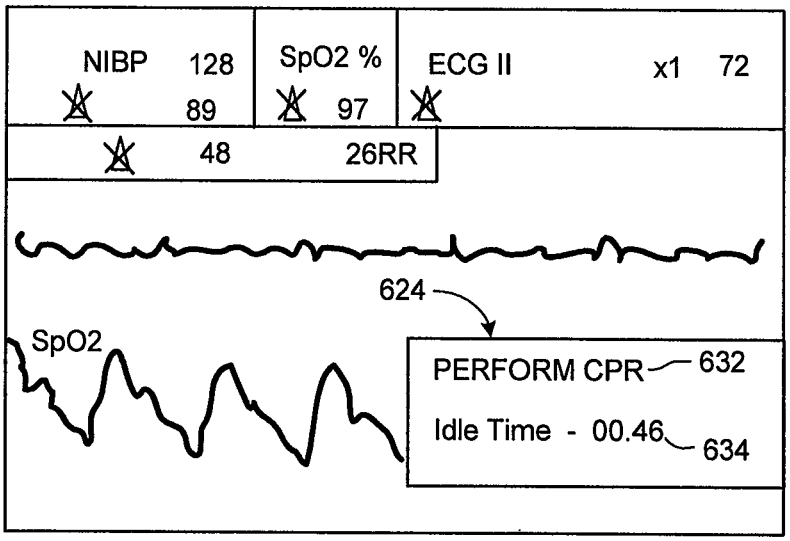
Figure 6C:
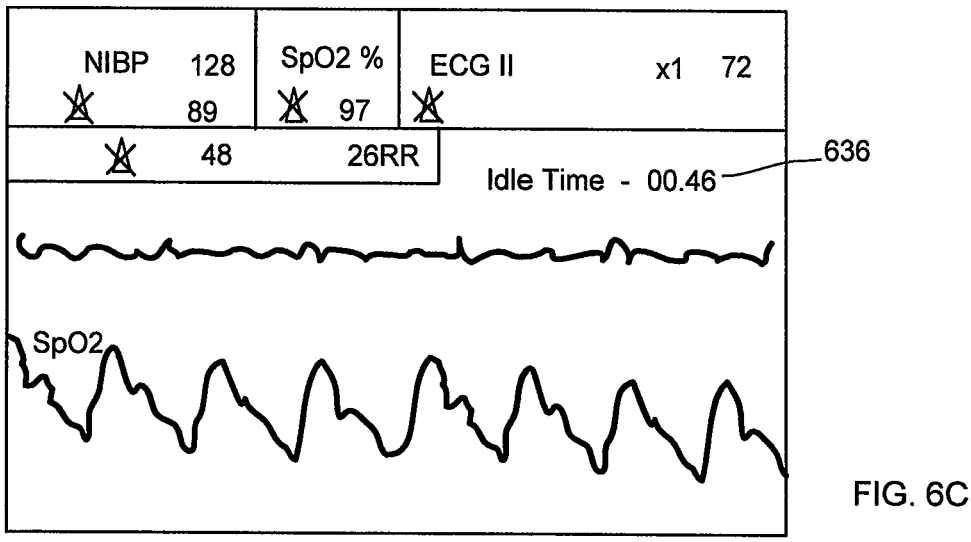

FIGS. 6A-6C show example screens that may be displayed to a rescuer on a defibrillator. Each of the displays may be supplemented with a display like box 522 in FIG. 5B when the defibrillator determines that rescuers providing a certain component of care (e.g., chest compressions) should be changed.

FIG. 6A shows exemplary information displayed during the administration of CPR chest compressions, while FIGS. 6B and 6C show exemplary information displayed when CPR chest compressions are not being sensed by the defibrillator. The defibrillator automatically switches the information presented based on whether chest compressions are detected. An exemplary modification of the information presented on the display can include automatically switching one or more waveforms that the defibrillator displays. In one example, the type of measurement displayed can be modified based on the presence or absence of chest compressions. For example, CO2 or depth of chest compressions may be displayed (e.g., a CO2 waveform 620 is displayed in FIG. 6A) during CPR administration, and upon detection of the cessation of chest compressions, the waveform can be switched to display an SpO2 or pulse waveform (e.g., an SpO2 waveform 622 is displayed in FIG. 6B).

Another exemplary modification of the information presented on the display can include automatically adding/removing the CPR information from the display upon detection of the presence or absence of chest compressions. As shown in FIG. 6A, when chest compressions are detected, a portion 624 of the display includes information about the CPR such as depth 626, rate 628, and PPI 630. As shown in FIG. 6B, when CPR is halted and the system detects the absence of CPR chest compressions, the defibrillator changes the CPR information in the portion 624 of the display, to include an indication 632 that the rescuer should resume CPR, and an indication 634 of the idle time since chest compressions were last detected. In a similar manner, when the defibrillator determines that rescuers should change, the label 632 can change to a message such as "Change Who is Administering CPR." In other examples, as shown in FIG. 6C, when CPR is halted, the defibrillation device can remove the portion of the display 624 previously showing CPR data and can display a full view of the second waveform. Additionally, information about the idle time 636 can be presented on another portion of the display.

Figure 7A:
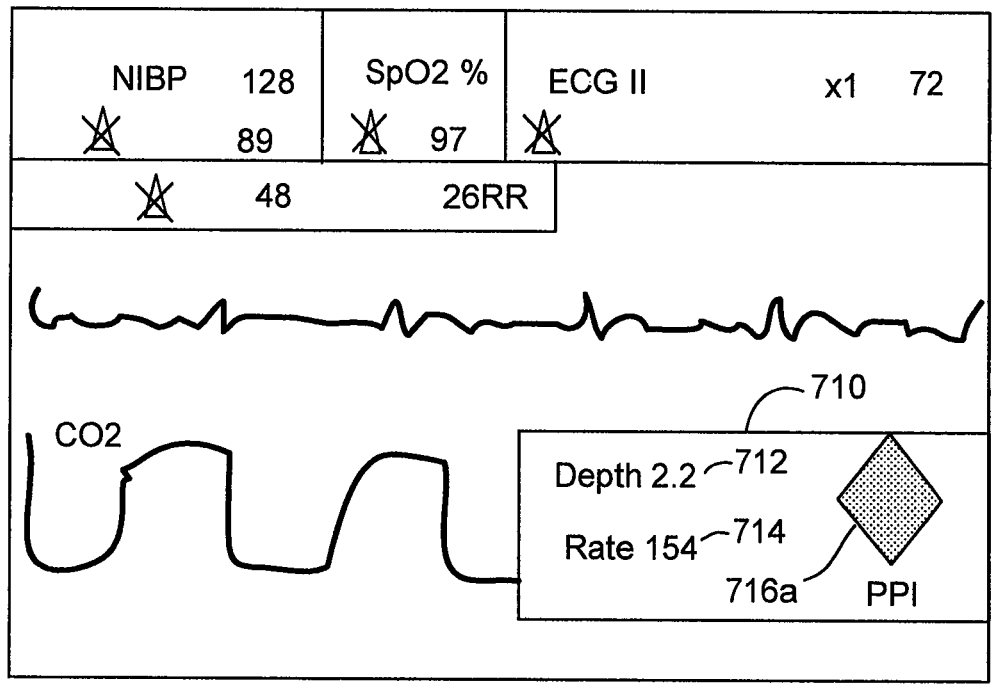
FIGS. 7A and 7B show screenshots providing feedback regarding a perfusion index created form chest compressions.
Figure 7B:
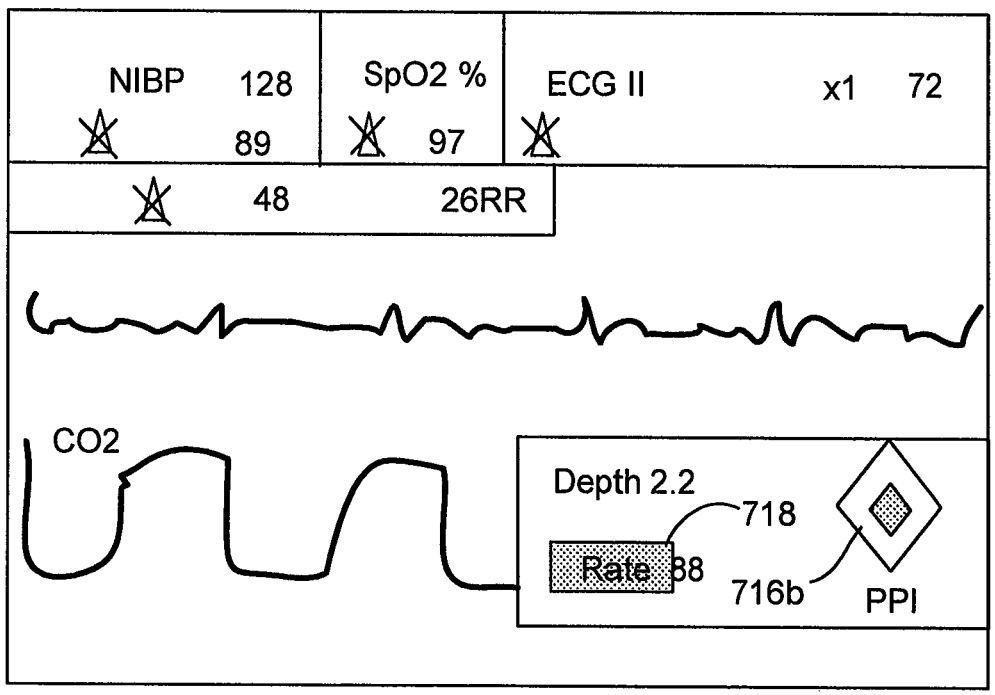

FIGS. 7A and 7B show defibrillator displays that indicate to a rescuer levels of perfusion being obtained by chest compressions that the rescuer is performing. FIG. 7A shows exemplary data displayed during the administration of CPR chest compressions when the CPR quality is within acceptable ranges, while FIG. 7B shows modifications to the display when the CPR quality is outside of the acceptable range.

In the example shown in FIG. 7B, the rate of chest compressions has dropped from 154 compressions per minute (FIG. 7A) to 88 compressions per minute. The defibrillator device determines that the compression rate of 88 compressions per minute is below the acceptable range of greater than 100 compressions per minute. In order to alert the user that the compression rate has fallen below the acceptable range, the defibrillator device provides a visual indication 718 to emphasize the rate information. In this example, the visual indication 718 is a highlighting of the rate information. Similar visual indications can be provided based on depth measurements when the depth of the compressions is shallower or deeper than an acceptable range of depths. Also, when the change in rate or depth indicates that a rescuer is becoming fatigued, the system may display a message to switch who is performing the chest compressions, and may also emit aural or haptic feedback to the same effect.

In the examples shown in FIGS. 7A and 7B, a perfusion performance indicator (PPI) 716 provides additional information about the quality of chest compressions during CPR. The PPI 716 includes a shape (e.g., a diamond) with the amount of fill in the shape differing based on the measured rate and depth of the compressions. In FIG. 7A, the depth and rate fall within the acceptable ranges (e.g., at least 100 compressions/minute (CPM) and the depth of each compression is greater than 1.5 inches) so the PPI indicator 716a shows a fully filled shape. In contrast, in FIG. 7B, when the rate has fallen below the acceptable range, the amount of fill in the indicator 716b is lessened such that only a portion of the indicator is filled. The partially filled PPI 716b provides a visual indication of the quality of the CPR is below an acceptable range.

As noted above with respect to FIG. 5A, in addition to measuring information about the rate and depth of CPR chest compressions, in some examples the defibrillator provides information about whether the rescuer is fully releasing his/her hands at the end of a chest compression. For example, as a rescuer tires, the rescuer may begin leaning on the victim between chest compressions such that the chest cavity is not able to fully expand at the end of a compression. If the rescuer does not fully release between chest compressions the quality of the CPR can diminish. As such, providing a visual or audio indication to the user when the user does not fully release can be beneficial. In addition, such factors may be included in a determination of whether the rescuer's performance has deteriorated to a level that the rescuer should be instructed to permit someone else perform the chest compressions, and such information may be conveyed in the various manners discussed above.

Figure 8A:
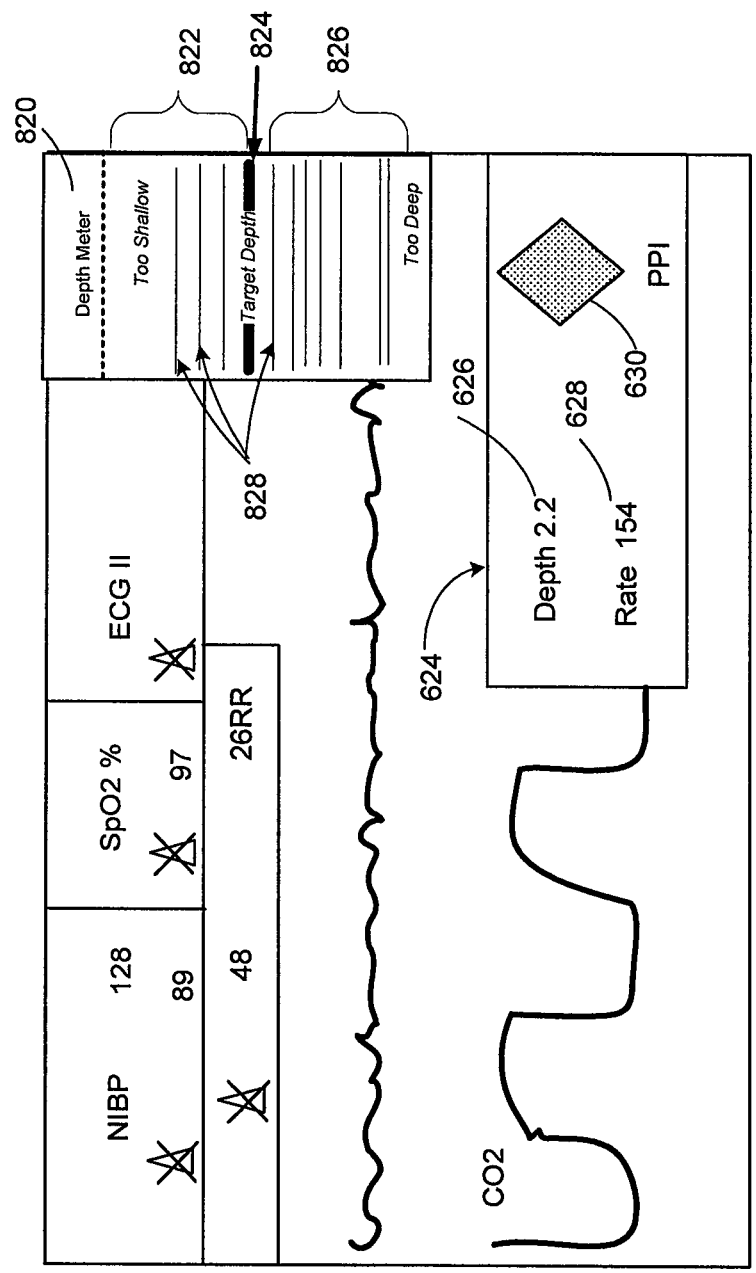
FIGS. 8A and 8B show screenshots with gradiated scales indicating target chest compression depths.

As shown in FIG. 8A, a visual representation of CPR quality can include an indicator of CPR compression depth such as a CPR depth meter 820. The CPR depth meter 820 can be automatically displayed upon detection of CPR chest compressions.

On the CPR depth meter 820, depth bars 828 visually indicate the depth of the administered CPR compressions relative to a target depth 824. As such, the relative location of the depth bars 828 in relation to the target depth 824 can serve as a guide to a rescuer for controlling the depth of CPR compressions. For example, depth bars 828 located in a region 822 above the target depth bar 824 indicate that the compressions were shallower than the target depth, and depth bars 828 located in a region 826 below the target depth bar 824 indicate that the compressions were deeper than the target depth. Again, then depth is inadequate (along with perhaps other factors) for a sufficient time to indicate that the rescuer is fatiguing, an indicator to switch rescuers may be provided in the manners discussed above.

Figure 8B:
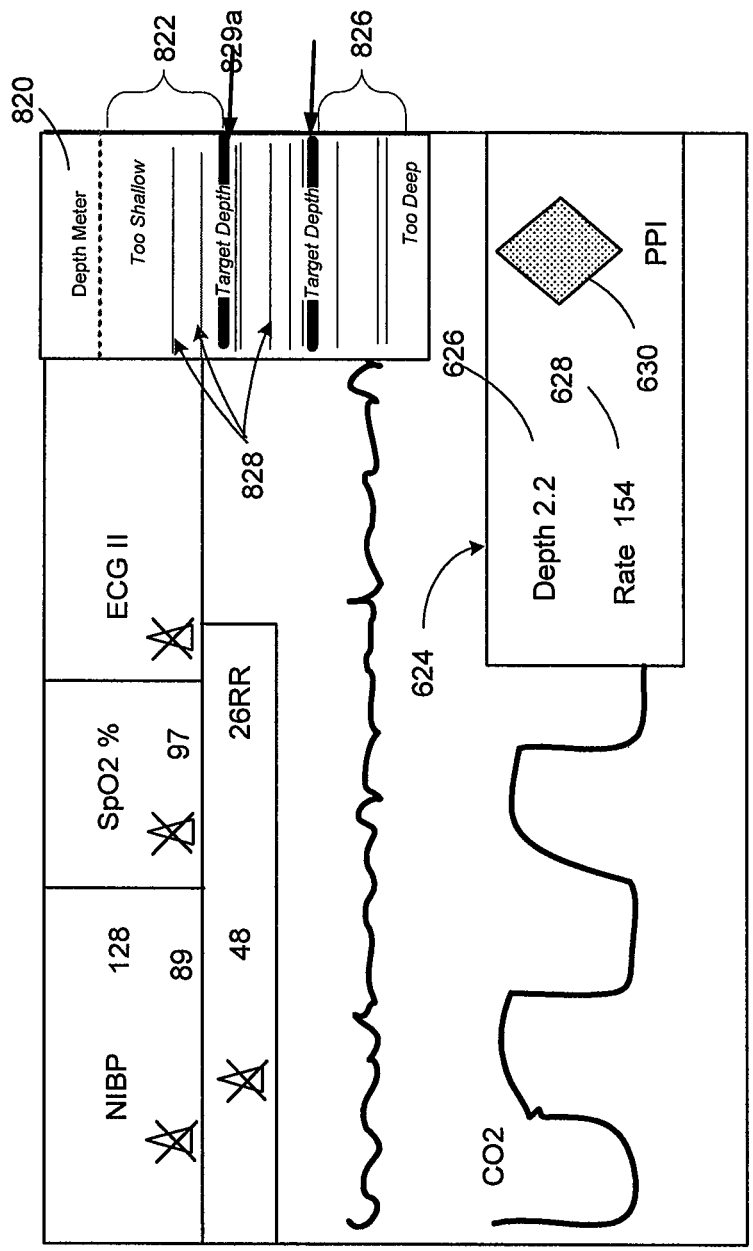

While the example shown in FIG. 8A displayed the target depth 824 as a single bar, in some additional examples, the target depth can be displayed as a range of preferred depths. For example, two bars 829a and 829b can be included on the depth meter 820 providing an acceptable range of compression depths (e.g., as shown in FIG. 8B). Additionally, in some examples, compressions that have depths outside of an acceptable range can be highlighted in a different color than compressions that have depths within the acceptable range of compression depths.

The depth bars 828 displayed on the CPR depth meter 820 can represent the compression depths of the most recent CPR compressions administered by the rescuer. For example, the CPR depth meter 820 can display depth bars 828 for the most recent 10-20 CPR compressions (e.g., the most recent 10 CPR compressions, the most recent 15 compressions, the most recent 20 CPR compressions). In another example, CPR depth meter 820 can display depth bars 828 for CPR compressions administered during a particular time interval (e.g., the previous 10 seconds, the previous 20 seconds).

In some additional embodiments, physiological information (e.g., physiological information such as end-tidal $CO_2$ information, arterial pressure information, volumetric CO2, pulse oximetry (presence of amplitude of waveform possibly), and carotid blood flow (measured by Doppler) can be used to provide feedback on the effectiveness of the CPR delivered at a particular target depth. Based on the physiological information, the system can automatically determine a target CPR compression depth (e.g., calculate or look-up a new CPR compression target depth) and provide feedback to a rescuer to increase or decrease the depth of the CPR compressions. Thus, the system can provide both feedback related to how consistently a rescuer is administering CPR compressions at a target depth, and feedback related to whether the target depth should be adjusted based on measured physiological parameters. If the rescuers does not respond to such feedback and continues performed sub-optimal CPR, the system may then display an additional message to switch out the person performing CPR chest compressions.

In some examples, the system regularly monitors and adjusts the target CPR compression depth. In order to determine a desirable target depth, the system makes minor adjustments to the target CPR compression depth and observes how the change in compression depth affects the observed physiological parameters before determining whether to make further adjustments to the target compression depth. More particularly, the system can determine an adjustment in the target compression depth that is a fraction of an inch and prompt the rescuer to increase or decrease the compression depth by the determined amount. For example, the system can adjust the target compression depth by 0.1-0.25 inches (e.g., 0.1 inches to 0.15 inches, 0.15 to 0.25 inches, about 0.2 inches) and provide feedback to the rescuer about the observed compression depth based on the adjusted target compression depth. Then, over a set period of time, the system can observe the physiological parameters and, based on trends in the physiological parameters without making further adjustments to the target compression depth and at the end of the set time period, may determine whether to make further adjustments to the target compression depth.

And again, the actual performance of the rescuer against the revised target may be continually monitored to determine when the rescuer's performance has fallen below an acceptable level, so that the rescuer and perhaps others may be notified to change who is performing the chest compressions. Also, each of the relevant parameters of patient condition discussed above with respect to the various screenshots may be made one of multiple inputs to a process for determining when rescuers who are performing one component of a rescue technique should be switched out with another rescuer, such as for reasons of apparent fatigue on the part of the first rescuer.

While at least some of the embodiments described above describe techniques and displays used during manual human-delivered chest compressions, similar techniques and displays can be used with automated chest compression devices such as the AUTOPULSE device manufactured by ZOLL Medical, MA.

Figure 9:
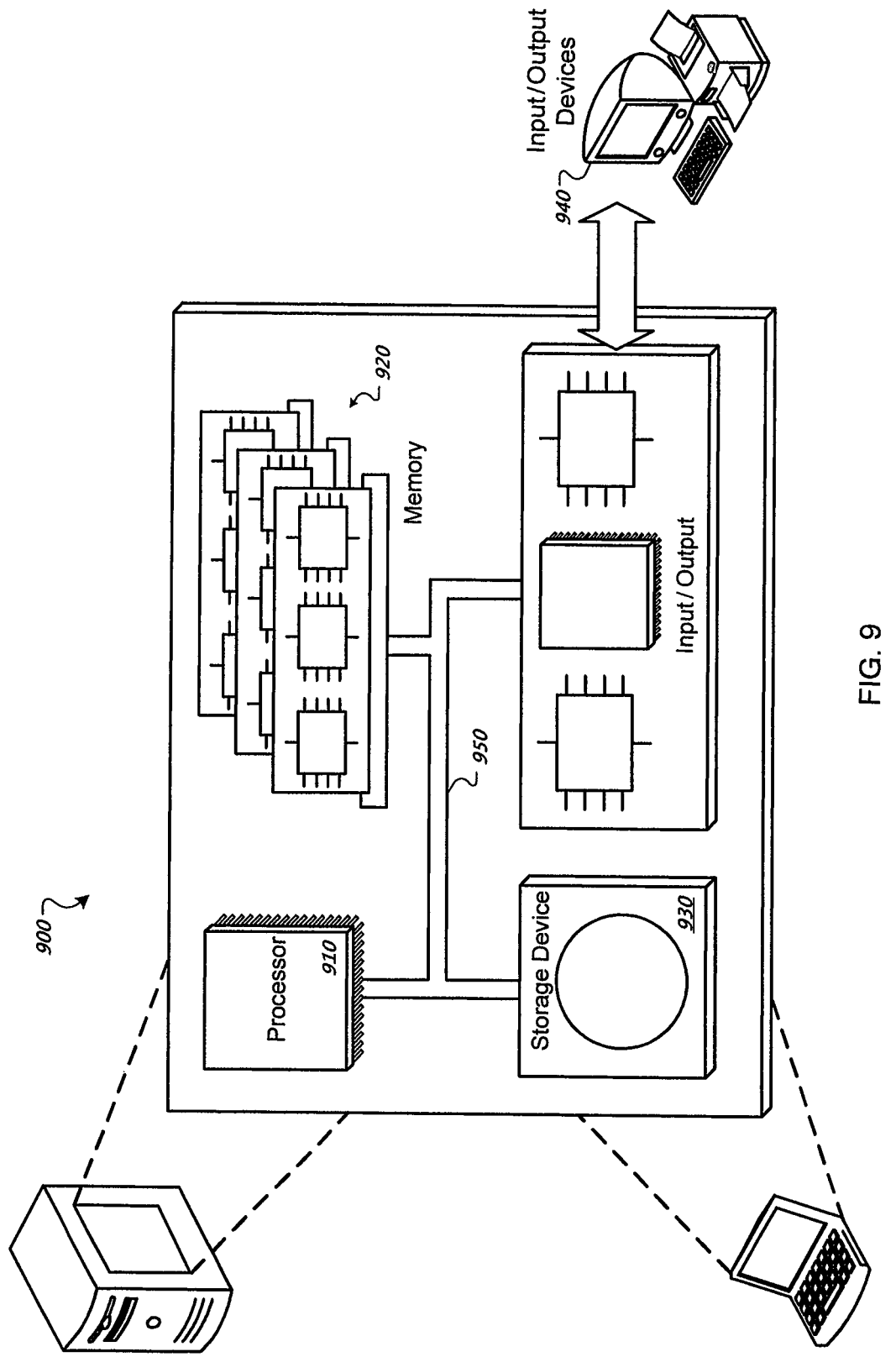
FIG. 9 shows a general computer system that can provide interactivity with a user of a medical device, such as feedback to a user in the performance of CPR.

The particular techniques described here may be assisted by the use of a computer-implemented medical device, such as a defibrillator that includes computing capability. Such defibrillator or other device is shown in FIG. 9, and may communicate with and/or incorporate a computer system 800 in performing the operations discussed above, including operations for computing the quality of one or more components of CPR provided to a victim and generating feedback to rescuers, including feedback to change rescuers who are performing certain components of the CPR. The system 900 may be implemented in various forms of digital computers, including computerized defibrillators laptops, personal digital assistants, tablets, and other appropriate computers. Additionally the system can include portable storage media, such as, Universal Serial Bus (USB) flash drives. For example, the USB flash drives may store operating systems and other applications. The USB flash drives can include input/output components, such as a wireless transmitter or USB connector that may be inserted into a USB port of another computing device.

The system 900 includes a processor 910, a memory 920, a storage device 930, and an input/output device 940. Each of the components 910, 920, 930, and 940 are interconnected using a system bus 950. The processor 910 is capable of processing instructions for execution within the system 900. The processor may be designed using any of a number of architectures. For example, the processor 910 may be a CISC (Complex Instruction Set Computers) processor, a RISC (Reduced Instruction Set Computer) processor, or a MISC (Minimal Instruction Set Computer) processor.

In one implementation, the processor 910 is a single-threaded processor. In another implementation, the processor 910 is a multi-threaded processor. The processor 910 is capable of processing instructions stored in the memory 920 or on the storage device 930 to display graphical information for a user interface on the input/output device 940.

The memory 920 stores information within the system 900. In one implementation, the memory 920 is a computer-readable medium. In one implementation, the memory 920 is a volatile memory unit. In another implementation, the memory 920 is a non-volatile memory unit.

The storage device 930 is capable of providing mass storage for the system 900. In one implementation, the storage device 930 is a computer-readable medium. In various different implementations, the storage device 930 may be a floppy disk device, a hard disk device, an optical disk device, or a tape device.

The input/output device 940 provides input/output operations for the system 900. In one implementation, the input/output device 940 includes a keyboard and/or pointing device. In another implementation, the input/output device 940 includes a display unit for displaying graphical user interfaces.

The features described can be implemented in digital electronic circuitry, or in computer hardware, firmware, software, or in combinations of them. The apparatus can be implemented in a computer program product tangibly embodied in an information carrier, e.g., in a machine-readable storage device for execution by a programmable processor; and method steps can be performed by a programmable processor executing a program of instructions to perform functions of the described implementations by operating on input data and generating output. The described features can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors of any kind of computer. Generally, a processor will receive instructions and data from a read-only memory or a random access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

To provide for interaction with a user, the features can be implemented on a computer having an LCD (liquid crystal display) or LED display for displaying information to the user and a keyboard and a pointing device such as a mouse or a trackball by which the user can provide input to the computer.

The features can be implemented in a computer system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include a local area network ("LAN"), a wide area network ("WAN"), peer-to-peer networks (having ad-hoc or static members), grid computing infrastructures, and the Internet.

The computer system can include clients and servers. A client and server are generally remote from each other and typically interact through a network, such as the described one. The relationship of client and server arises by virtue of computer programs running on the respective computers and having a client-server relationship to each other.

Many other implementations other than those described may be employed, and may be encompassed by the following claims.

What is claimed is:

1. A system for managing cardiopulmonary resuscitation (CPR) treatment to a person in need of emergency assistance, the system comprising:
   a chest compression assembly configured to be placed on a chest of the person in need of emergency assistance, the chest compression assembly comprising:
   a housing upon which a rescuer places his/her hands to provide CPR to the person in need of emergency assistance;
   one or more sensors positioned within the housing and adapted to measure information indicative of CPR being provided to the person in need of emergency assistance;
   a sensor interface configured to receive input from one or more sensors adapted to measure information indicative of CPR being provided to the person in need of emergency assistance; and
   a haptic vibrator positioned within the housing and configured to generate a pattern of haptic feedback for the rescuer while the chest compression assembly is being placed on the chest; and
   a processing circuitry operatively coupled with the sensor interface and in communication with the haptic vibrator, the processing circuitry configured to:
   receive input from the one or more sensors,
   generate an indication of quality of the CPR being provided to the person in need of emergency assistance based the input from the one or more sensors,
   determine whether the indication of quality of the CPR falls within an acceptable range based on one or more target CPR parameters, and
   generate the pattern of haptic feedback with the haptic vibrator when the indication of quality of the CPR falls outside of the acceptable range as a prompt to switch the rescuer with another rescuer performing CPR.

2. The system of claim 1, further comprising an output interface that is configured to generate at least one of audible feedback and visual feedback based on the indication of the quality of the CPR.

3. The system of claim 1, wherein the sensor interface is configured to receive input from an accelerometer.

4. The system of claim 1, wherein the one or more target CPR parameters include at least one of a chest compression parameter and a ventilation parameter.

5. The system of claim 4, wherein the chest compression parameter is based on at least one of chest compression depth and chest compression rate.

6. The system of claim 1, wherein the indication of quality of the CPR includes a quality score of the CPR administered to the person in need of emergency assistance.

7. The system of claim 6, wherein the indication of quality of the CPR includes a determination of whether the quality score falls within the acceptable range based on the one or more target CPR parameters.

8. The system of claim 6, wherein the quality score is indicative of an instantaneous quality of CPR administered to the person in need of emergency assistance.

9. The system of claim 6, wherein the quality score is indicative of an average quality of CPR administered to the person in need of emergency assistance.

10. The system of claim 1, further comprising defibrillation electrodes coupled to the chest compression assembly.

11. The system of claim 10, wherein the defibrillation electrodes and the chest compression assembly are coupled together via a wiring harness.

12. The system of claim 10, wherein the defibrillation electrodes and the chest compression assembly are adapted to be operatively connected with a defibrillator.

13. The system of claim 12, wherein the defibrillation electrodes and the chest compression assembly are adapted to be operatively connected with the defibrillator via a wire.

14. The system of claim 1, wherein the haptic vibrator is arranged so as to rest adjacent the rescuer's hands during performance of CPR chest compressions.

15. The system of claim 1, wherein the one or more sensors include at least one accelerometer.

16. The system of claim 1, wherein a lower side of the housing comprises an adhesive configured to adhere to the chest of the person in need of emergency assistance, thereby coupling the chest compression assembly to the chest of the person in need of emergency assistance.

17. The system of claim 1, wherein a continuous vibration provided as the pattern of haptic feedback provides the prompt to switch the rescuer with the other rescuer performing CPR.

18. The system of claim 1, wherein the pattern of haptic feedback is provided to guide the rescuer in performing CPR.

19. The system of claim 1, wherein the indication of quality of the CPR is based on a calculation of an indication of the rescuer's fatigue.

20. The system of claim 19, wherein the indication of the rescuer's fatigue is based at least in part on at least one of chest compression depth and chest compression rate.

21. The system of claim 1, further comprising a memory operatively connected to the processing circuitry and configured to store a plurality of signals providing prompts related to CPR.

22. The system of claim 21, wherein the prompt to switch the rescuer with the other rescuer performing CPR is selected from the plurality of signals providing prompts related to CPR stored in the memory.

23. The system of claim 21, wherein the plurality of signals providing prompts related to CPR stored in memory comprise a prompt related to rate of compressions, a prompt related to depth of compressions, prompts related to an ECG waveform, prompts related to a $CO_2$ waveform, a perfusion performance indicator, the prompt to switch the rescuer with the other rescuer performing CPR, or any combination thereof.

\* \* \* \* \*